(12) United States Patent
Hayashi et al.

(10) Patent No.: US 7,326,806 B2
(45) Date of Patent: Feb. 5, 2008

(54) CATALYST FOR THE PREPARATION OF CARBOXYLIC ESTERS AND METHOD FOR PRODUCING CARBOXYLIC ESTERS

(75) Inventors: Toshio Hayashi, Kobe (JP); Takahiro Inagaki, Hirakata (JP)

(73) Assignee: Nippon Shokubai Co., Ltd., Osaka-fu (JP)

( * ) Notice: Subject to any disclaimer, the term of this patent is extended or adjusted under 35 U.S.C. 154(b) by 166 days.

(21) Appl. No.: 10/162,040

(22) Filed: Jun. 3, 2002

(65) Prior Publication Data
US 2003/0060655 A1    Mar. 27, 2003

(30) Foreign Application Priority Data

Jun. 4, 2001   (JP) ............................. 2001-167739
Sep. 26, 2001  (JP) ............................. 2001-294233

(51) Int. Cl.
C07C 67/00    (2006.01)
(52) U.S. Cl. .................................... 560/208
(58) Field of Classification Search ............... 560/205, 560/210, 231, 232, 239; 502/344
See application file for complete search history.

(56) References Cited

U.S. PATENT DOCUMENTS

| | | | |
|---|---|---|---|
| 4,249,019 A | | 2/1981 | Tamura et al. |
| 4,518,796 A | | 5/1985 | Aoshima et al. |
| 4,877,898 A | | 10/1989 | Paparizos et al. |
| 5,334,751 A | * | 8/1994 | Lemanski et al. ........... 560/265 |
| 6,040,472 A | * | 3/2000 | Yamamatsu et al. ........ 560/210 |
| 6,124,505 A | * | 9/2000 | Haruta et al. ................ 568/360 |
| 6,528,088 B1 | | 3/2003 | Gilleland et al. |
| 6,656,493 B2 | | 12/2003 | Dzija et al. |

2003/0099692 A1   5/2003   Lydzinski et al.

FOREIGN PATENT DOCUMENTS

| | | |
|---|---|---|
| CA | 1278312 | 12/1990 |
| EP | 0 199 530 A2 | 10/1986 |
| EP | 0 773 062 A1 | 5/1997 |
| EP | 0 965 383 A1 | 12/1999 |
| JP | 55-153740 | 11/1980 |
| JP | 61-243044 | 10/1986 |
| JP | 04-300851 | 10/1992 |
| JP | 05-236885 | 9/1993 |
| JP | 10-028865 | 2/1998 |
| JP | 2000-154164 | 6/2000 |
| JP | 2001-131122 | 5/2001 |
| JP | 2001-162162 | 6/2001 |
| WO | WO 00/09259 | 2/2000 |
| WO | WO 00/61535 | 10/2000 |

OTHER PUBLICATIONS

"Synthesis of Ethyl Acetate from Ethanol in the Presence of Metallic Palladium Catalyst," Kogyo Kagaku (Industrial Chemistry), p. 1517-1522. vol. 71, No. 9, 1968 with partial translation.
Supplementary European Search Report, Jul. 9, 2007, from corresponding European Patent Application Serial No. EP 02 73 3287.

* cited by examiner

*Primary Examiner*—Karl Puttlitz
(74) *Attorney, Agent, or Firm*—Knobbe, Martens, Olson & Bear, LLP

(57) ABSTRACT

It is an object of the present invention to provide a catalyst for manufacturing a carboxylic ester, which has superior catalytic activity. The present invention relates to a catalyst for preparing a carboxylic ester, used in a) a reaction for preparing a carboxylic ester by reacting oxygen, an aldehyde, and an alcohol, or b) a reaction for manufacturing a carboxylic ester by reacting oxygen and one or more types of alcohol, comprising a carrier and 1) ultrafine gold particles and/or 2) ultrafine metal particles containing gold and a second element other than gold, having an average particle diameter of not more than 6 nm, are supported on the carrier.

11 Claims, No Drawings

US 7,326,806 B2

CATALYST FOR THE PREPARATION OF CARBOXYLIC ESTERS AND METHOD FOR PRODUCING CARBOXYLIC ESTERS

TECHNICAL FIELD

This invention relates to a catalyst for the preparation of carboxylic esters, and to a method for producing carboxylic esters.

BACKGROUND ART

One known method for manufacturing a carboxylic ester from an aldehyde involves first manufacturing a carboxylic acid by oxidizing an aldehyde, and then reacting this carboxylic acid with an alcohol. The problem with this method, though, is that the reaction consists of two steps, so the equipment cost is high, and furthermore the yield is inadequate in the step of oxidizing the aldehyde. In particular, in the manufacture of methacrylic acid by the oxidation of methacrolein, the selectivity is only about 80% at best, so the space-time yield of the targeted product is low, and a large multi-tube type of reactor is required.

One attempt at solving this problem has been to react an aldehyde and an alcohol in the presence of oxygen. For example, it has been reported that ethyl acetate is obtained by oxidizing ethanol in the presence of a metallic palladium catalyst (Kogyo Kagaku [Industrial Chemistry], Vol. 71, 1515 (1968)). According to this report, the reaction mechanism is such that the acetaldehyde produced by the oxidation of ethanol reacts with the ethanol as a result of the palladium catalyst, giving ethyl acetate.

A method has also been proposed for applying these oxidative esterification reactions to α,β-unsaturated aldehydes to manufacture α,β-unsaturated carboxylic esters. For instance, U.S. Pat. No. 4,249,019 discloses a method for manufacturing α,β-unsaturated carboxylic esters by reacting an aldehyde and an alcohol in the presence of a catalyst composed of the following three components: (1) palladium, (2) at least one member of the group consisting of lead, thallium, and mercury, and (3) at least one member of the group consisting of alkali metals and alkaline earth metals. U.S. Pat. No. 4,518,796 discloses a method for manufacturing α,β-unsaturated carboxylic esters by reacting the above-mentioned components in the presence of a catalyst composed of an intermetallic compound composed of palladium and bismuth.

Another known method for manufacturing carboxylic esters involves reacting an aldehyde with an alcohol in the presence of a catalyst comprising gold supported on a hydrophobic carrier such as activated carbon (Unexamined Japanese Patent Publication 2000-154164).

Meanwhile, methods in which a carboxylic ester is manufactured using an alcohol as the starting raw material in the presence of oxygen are also known. For instance, a method has been proposed in which an intermetallic compound including palladium and at least one member of the group consisting of lead, mercury, thallium, and bismuth is used as a catalyst (Japanese Patent Publication S62-7903).

However, the catalysts discussed in prior art all have low catalytic activity, and there is a need for further improvement in order to manufacture carboxylic esters more efficiently.

DISCLOSURE OF THE INVENTION

A primary object of the present invention is to provide a catalyst for producing a carboxylic ester, which has superior catalytic activity.

As a result of diligent research aimed at solvent the problems encountered with prior art, the inventors arrived at the present invention upon discovering that the object can be achieved by using specific materials.

Specifically, the present invention relates to a catalyst for manufacturing carboxylic esters and to a method for manufacturing carboxylic esters, as follows.

1. A catalyst for preparing carboxylic esters, used in a) a reaction for preparing a carboxylic ester by reacting oxygen, an aldehyde, and an alcohol, or b) a reaction for preparing a carboxylic ester by reacting oxygen and one or more types of alcohol, which comprises a carrier and 1) ultrafine gold particles and/or 2) ultrafine metal particles containing gold and a second element other than gold, said particles having an average particle diameter of no more than 6 nm, said particles being supported on the carrier.

2. The catalyst for the preparation of carboxylic esters according to 1 above, wherein the second element is at least one member of the group consisting of elements in groups 2B, 3B, 4B, 5B and 6B of the fourth to sixth periods of the Periodic Table, and group 8 of the fourth period of the Periodic Table.

3. The catalyst for preparing carboxylic esters according to 1 above, wherein the carrier is an inorganic oxide.

4. The catalyst for preparing carboxylic esters according to 1 above, wherein the carrier is composed of an oxide including at least one member of the group consisting of silicon, magnesium, calcium, strontium, barium, aluminum, titanium, vanadium, chromium, manganese, iron, cobalt, nickel, copper, zinc, zirconium, niobium, tin, lead, lanthanum and cerium.

5. A method for producing carboxylic esters by reacting oxygen, an aldehyde, and an alcohol in the presence of the catalyst for preparing carboxylic esters according to any of claims 1 to 4.

6. The producing method according to 5 above, wherein the aldehyde is at least one member of the group consisting of acrolein and methacrolein, and the alcohol is at least one member of the group consisting of $C_1$ to $C_4$ primary alcohols.

7. The producing method according to 5 above, wherein the aldehyde is at least one member of the group consisting of glyoxal and pyruvic aldehyde, and the alcohol is at least one member of the group consisting of $C_1$ to $C_4$ primary alcohols.

8. A method for producing carboxylic esters by reacting oxygen and one or more types of alcohol in the presence of the catalyst for preparing carboxylic esters according to any of 1 to 4 above.

9. The producing method according to 8 above, wherein the alcohol includes ethylene glycol or 1,2-propylene glycol as an essential component.

The catalyst for manufacturing a carboxylic ester and the method for manufacturing a carboxylic ester of the present invention will now be described in detail.

1. Catalyst for the Preparation of Carboxylic Esters

The catalyst for preparing a carboxylic ester of the present invention is used in a) a reaction for preparing a carboxylic ester by reacting oxygen, an aldehyde, and an alcohol, or b) a reaction for preparing a carboxylic ester by reacting oxygen and one or more types of alcohol, which comprises (A) a catalyst carrier and (B) 1) ultrafine gold particles and/or 2) ultrafine metal particles containing gold and a second element other than gold, the particles having an average particle diameter of no more than 6 nm, the particles are supported on the carrier. The above-mentioned 1) ultrafine gold particles and the above-mentioned 2) ultrafine metal particles will sometimes referred to collectively as "particles of the present invention."

The particles of the present invention have an average diameter of 6 nm or less, with 5 nm or less being particularly favorable. Keeping the average particle diameter to 6 nm or less allows better catalytic activity to be achieved. There are no particular restrictions on the lower limit to the average particle diameter, but about 1 nm is probably best from the standpoint of physical stability. The "average particle diameter" of the particles of the present invention indicates the calculated average diameter for 100 particles, obtained by subtracting 1) the ten largest particles and 2) the ten smallest particles out of 120 particles selected arbitrarily in a micrograph of the particles on the carrier produced by transmission electron microscope (TEM). The maximum values for the particle size distribution of the particles of the present invention may be between 1 and 6 nm, and particularly between 1 and 5 nm. It is better for the particle size distribution to be narrower, and it is preferable for the standard deviation of the diameter of the above-mentioned 120 particles to be no more than 2, with 1.5 or less being particularly favorable.

The above-mentioned 1) ultrafine gold particles are substantially composed of gold. Other elements or impurities may be contained as long as the effect of the present invention is not compromised.

The above-mentioned 2) ultrafine metal particles are primarily composed of at least gold (as the first element) and a second element other than gold. It is preferable for each of the individual ultrafine metal particles to contain both the first element and the second element. Also, as long as the specified effect of the present invention can be obtained, the gold and the second element may form an alloy or intermetallic compound. Other elements or impurities besides the gold and the second element may be contained as long as the effect of the present invention is not compromised.

An element other than palladium is preferable as the above-mentioned second element, and in particular at least one member of the group consisting of elements in groups 2B, 3B, 4B, 5B, and 6B of the fourth to sixth periods and group 8 of the fourth period of the Periodic Table ("Kagaku Bunseki Binran [Handbook of Chemical Analysis], Revised Fifth Edition," Maruzen (2001)) can be used favorably. Specific examples of group 2B (zinc family) include zinc, cadmium, and mercury, those of group 3B (boron family) include gallium, indium, and thallium, those of group 4B (carbon family) include germanium, tin, and lead, those of group 5B (nitrogen family) include arsenic, antimony, and bismuth, those of group 6B (oxygen family) include selenium, tellurium, and polonium, and those of group 8 (iron family) include iron, cobalt, and nickel. It is preferable for at least lead to be included as the second element. For example, a catalyst in which metal particles including lead and gold are supported on a carrier can be used to advantage as the catalyst of the present invention.

Any commercially available carrier or one that has been used in the past as a catalyst carrier in the manufacture of carboxylic esters can be used with no particular restrictions thereon. Any carrier or support produced by a known method can also be used. Examples include metal oxides (such as silica, alumina, titania, zirconia, or magnesia), mixed oxides (such as silica-alumina, titania-silica, or silica-magnesia), zeolites (such as ZSM-5), mesoporous silicates (such as MCM-41), natural minerals (such as clay, diatomaceous earth, or pumice), carbon materials (such as activated carbon or graphite), and various other carriers or supports.

An inorganic oxide carrier is preferable with the present invention. Particularly favorable is the use of an inorganic oxide carrier composed of an oxide including at least one member of the group consisting of silicon, magnesium, calcium, strontium, barium, aluminum, silicon, titanium, vanadium, chromium, manganese, iron, cobalt, nickel, copper, zinc, zirconium, niobium, tin, lead, lanthanum and cerium. The above-mentioned oxide may be a mixed oxide comprising a mixture of two or more oxides of single elements, or it may be a double oxide (or mixed oxide).

An oxide including silicon and one or more members of the group consisting of magnesium, calcium, strontium, barium, aluminum, titanium, vanadium, chromium, manganese, iron, cobalt, nickel, copper, zinc, zirconium, niobium, tin, lead, lanthanum, and cerium can be used favorably as the inorganic oxide carrier in the present invention.

There are no particular restrictions on the method for manufacturing the above-mentioned inorganic oxide carrier, and any known manufacturing method can be employed. Examples include impregnation, coprecipitation, ion exchange, vapor phase deposition, kneading and hydrothermal synthesis.

For instance, this inorganic oxide carrier is obtained by impregnating silica with an aqueous solution of a water-soluble compound including one or more members of the group consisting of magnesium, calcium, strontium, barium, aluminum, titanium, vanadium, chromium, manganese, iron, cobalt, nickel, copper, zinc, zirconium, niobium, tin, lead, lanthanum and cerium, and then calcing the impregnated product thus obtained. This inorganic oxide carrier allows the particles of the present invention (the component with catalytic activity) to be supported more securely in the form of ultrafine particles, so even higher catalytic activity can be obtained as a result of the synergistic effect with the particles of the present invention, and furthermore the physical stability of the ultrafine particles is enhanced, and particle growth (sintering) and release are prevented, which serves to extend the catalyst life.

There are no restrictions on the compounds used in the above-mentioned preparing method, but examples include nitrates, sulfates, hydroxides, and other such inorganic compounds, and carboxylates, alkoxides, acetylacetonates, and other such organic compounds.

Nor is the above-mentioned water-soluble compound limited, as long as it is water-soluble. Examples include zinc nitrate, lanthanum nitrate, iron nitrate, nickel nitrate, aluminum nitrate, and other such inorganic acid salts, and lead acetate, magnesium acetate, and other such organic acid salts. These salts may also be in the form of an anhydride or a hydrate. The concentration of the above-mentioned aqueous solution can be suitably determined according to the type of water-soluble compound being used and other factors.

There are no restrictions on the amount in which the above-mentioned aqueous solution impregnates the silica, but this amount usually may be about 1 to 20 weight parts per 100 weight parts of silica.

It is preferable for the carrier to be porous in the present invention. In particular, the specific surface area thereof (BET method) is usually at least 50 $m^2/g$, preferably at least 100 $m^2/g$. There are no limitations on the size or shape of the carrier, which may be suitably determined as dictated by the intended application of the final product.

The amount in which the particles of the present invention are supported may be suitably determined according to the intended application of the final product, the type of carrier, and so forth, but an amount of about 0.01 to 20 weight parts, and particularly 0.1 to 10 weight parts, per 100 weight parts of carrier is usually favorable.

In the case of the above-mentioned 2) ultrafine metal particles, there are no restrictions on the proportions in which gold and the second element are supported, as long as the supported amounts are within the range given above, but usually the atomic ratio of gold to the second element (gold:the second element) is about 1:0.01-100, with 1:0.1-10 being preferable, and 1:0.2-5 being especially good. Setting the ratio to within this range will afford even better catalytic activity.

There are no restrictions on the method for manufacturing the catalyst of the present invention as long as it allows the particles of the present invention to be supported. The loading or supporting method itself can be a known method such as coprecipitation, deposition-precipitation, impregnation, or vapor phase deposition. Coprecipitation, deposition-precipitation, or another such method can be used favorably as the loading method in the present invention, but deposition-precipitation is especially good. More specifically, ultrafine gold particles or metal particles can be supported by the following methods.

When the Above-mentioned 1) Ultrafine Gold Particles are Supported

In this case, for example, the catalyst of the present invention can be obtained by mixing a carrier with an aqueous solution of a water-soluble compound including gold, thereby depositing a precipitate containing gold on the carrier, and then calcing the recovered solids.

There are no restrictions on the above-mentioned water-soluble compound as long as it is water-soluble, but examples include tetrachloroauric (III) acid ($H(AuCl_4)$), sodium tetrachloroaurate (III) ($Na(AuCl_4)$), potassium dicyanoaurate (I) ($K(Au(CN)_2)$), diethylamine gold(III) trichloride (($C_2H_5)_2NH(AuCl_3)$), and other such complexes; and gold(I) cyanide and other such gold compounds. One or more types of these compounds can be used.

The gold concentration in the above-mentioned aqueous solution will vary with the type of compound being used and other factors, but usually may be about 0.1 to 100 mmol/L. The pH of the aqueous solution usually may be about 5 to 10, with a range of 6 to 9 being preferable. The pH can be adjusted to this range, for example, with sodium hydroxide, potassium hydroxide, sodium carbonate, potassium carbonate, ammonia, or another alkali. If needed, hydrochloric acid or another such acid can also be used. These alkalies and acids may be used in the form of aqueous solutions as needed.

A surfactant may also be added to the aqueous solution if necessary. The surfactant may be appropriately selected from among known and commercially available surfactants according to the above-mentioned aqueous solution. Examples include long chain alkylsulfonic acids and salts thereof, long chain alkylbenzenesulfonic acids and salts thereof, long chain alkylcarboxylic acids and salts thereof, arylcarboxylic acids and salts thereof, and other such anionic surfactants; long chain alkyl quaternary ammonium salts and other such cationic surfactants; and polyalkylene glycols, polyoxyethylene nonylphenols, and other such nonionic surfactants. One or more types of these surfactants may be used. In the present invention, an anionic surfactant or nonionic surfactant is preferred, with an anionic surfactant being particularly favorable. Among anionic surfactants, long chain alkylsulfonic acids with eight or more carbons and salts thereof, long chain alkylbenzenesulfonic acids with eight or more carbons and salts thereof, and arylcarboxylic acids and salts thereof are preferable, for example.

The amount in which the surfactant is used can be suitably determined according to the desired dispersibility, the type of surfactant being used, and other factors, but the concentration of the surfactant usually may be set to about 0.1 to 10 mmol/L.

The carrier that is mixed with the above-mentioned aqueous solution may be used in the form of granules, particles, etc. The amount in which the above-mentioned carrier is used may be suitably determined according to the concentration of the above-mentioned aqueous solution, the type of carrier being used, and other factors. In the mixing of the aqueous solution with the carrier, the aqueous solution may be heated as necessary. The temperature in this case usually may be about 30 to 100° C., and preferably 50 to 95° C.

Then, this carrier is mixed with an aqueous solution of a water-soluble compound including gold, after which the solids are recovered. There are no restrictions on the method for recovering the solids, but this can be accomplished, for example, by recovering the supernatant liquid, or by employing a known solid-liquid separation method. The recovered solids are preferably washed with ion exchange water or the like until there are substantially no remaining ions.

The above-mentioned solids (gold-fixed substance) are then calcined. Prior to calcination, the solids may also be heated and dried at a specific temperature if necessary. The drying temperature usually may be under 150° C. The calcination temperature may be usually about 150 to 800° C., with 200 to 700° C. being preferable, and 250 to 600° C. being best. The temperature may be suitably set within this range so that the specified ultrafine gold particles will be obtained. The calcination may be performed in air (atmospheric), in an oxidative atmosphere, in an inert gas atmosphere such as argon or helium, or in a reductive atmosphere such as hydrogen gas. The calcination time may be suitably determined according to the calcination temperature, the size of the solids, and so forth. This calcination yields the catalyst of the present invention.

When the Above-mentioned 2) Ultrafine Metal Particles are Supported

In this case, for example, the catalyst of the present invention can be obtained by heat treating a carrier including at least one member of the group consisting of gold and compounds thereof, and at least one member of the group consisting of a second element and compounds thereof. The gold compound or compound of the second element may each be a hydroxide, chloride, carboxylate, nitrate, alkoxide, acetylacetonate, or the like.

There are no restrictions on the order in which the gold and the second element are supported on the carrier, and either may be supported first, or both at the same time. Specifically, any of the following manufacturing methods A to C can be employed.

(A) The gold is supported on the carrier, and then the second element is supported.

(B) The second element is supported on the carrier, and then the is supported.

(C) The gold and the second element are supported simultaneously on the carrier.

Each of these methods will be described below.

Manufacturing Method A

The above-mentioned method A involves loading the gold on the carrier, and then loading the second element. First, a gold-loading carrier or a gold-containing carrier (a carrier on which gold is supported) is prepared. There are no restrictions on how this gold-loading carrier is prepared, and any conventional method can be applied, such as coprecipitation, deposition-precipitation, impregnation, or vapor phase deposition. Coprecipitation, deposition-precipitation, or another such method is preferred in the present invention, and deposition-precipitation is especially good. Specifically, the methods given in 1) above can be applied.

Then, at least one member of the group consisting of a second element and compounds thereof is supported on the gold-loading carrier, after which a heat treatment is performed to compound the gold with the second element. There are no restrictions on how this support is accomplished, and a conventional method can be employed. Examples include impregnation, ion exchange, and vapor phase deposition, of which impregnation is preferred. For instance, a solution in which a compound including the second element has been dissolved is mixed with the above-mentioned gold-loading carrier, after which the solids are recovered from this mixture and heat treated, which favorably supports the second element.

There are no particular restrictions on the compound that includes the second element, but examples include nitrates, sulfates, hydroxides, chlorides, and other such inorganic compounds, and formates, acetates, β-diketone compounds, alkoxides, and other such organic compounds. More specific examples include lead acetate, zinc acetate, zinc nitrate, bismuth nitrate, germanium(III) butoxide, nickel bisacetylacetonate, and iron acetate.

The solution in which the compound including the second element is dissolved can be prepared by using a combination of a compound including the second element and a solvent in which this compound will be dissolved. There are no particular restrictions on the solvent, but water, organic solvents, and the like can be used. Examples of organic solvents include alcohols, ketones, aromatic hydrocarbons, carboxylic esters, and nitriles. The use of water and one or more types of alcohol (particularly methanol and ethanol) is preferable. Therefore, it is preferable to use the above-mentioned compound that will dissolve in water or an alcohol for the above-mentioned combination. For example, when lead is used as the second element, a solution obtained by dissolving lead acetate in methanol can be used to advantage.

The concentration of the second element in the solution in which the compound including the second element is dissolved can be suitably determined according to the type of the above-mentioned compound, the type of solvent, and other factors, but usually may be about 0.01 to 10 mmol/L. The ratio in which the above-mentioned gold-loading carrier is mixed with the solution in which the compound including the second element is dissolved can be suitably determined according to the concentration of this solution, the desired amount in which the gold or second element is loaded or supported, and other factors.

After a mixture of the gold-loading carrier and the solution in which the compound including the second element is dissolved has been prepared, the solids are recovered from this mixture. There are no restrictions on how the solids are recovered, but an example is a method in which the compound including the second element is supported on the gold-loading carrier. It is preferable for the solvent to be distilled off with an evaporator or the like, for example.

Next, the solids are heat treated. The heat treatment temperature may be one that will allow the metal particles thus obtained so as to consist of gold and the second element. Specifically, the heat treatment may be such that, when the metal-containing composition ultimately obtained is used as a catalyst, the compounding of the gold and the second element results in catalytic activity.

This heat treatment temperature will vary with the type of second element and other factors, but is generally about 50 to 800° C., and preferably 100 to 600° C. The heat treatment time can be suitably adjusted by varying the heat treatment temperature and so forth, but usually may be about 10 minutes to 24 hours.

There are no particular restrictions on the heat treatment atmosphere, which may be a reductive, oxidative, or inert atmosphere, for example. A reductive atmosphere can be achieved, for instance, by using hydrogen, carbon monoxide, an alcohol, or another reductive gas, or by using a mixed gas in which one of these gases is diluted with an inert gas such as nitrogen, helium, or argon. An oxidative atmosphere can be achieved by using a gas containing oxygen, air, or the like. An inert atmosphere can be achieved by using an inert gas such as nitrogen, helium, or argon. The use of a reductive atmosphere is particularly favorable in the present invention. It is also possible to perform heat treatment in an oxidative atmosphere, followed by heat treatment in a reductive atmosphere.

Depending on the type of second element, the solids may also be subjected to a reduction treatment using formalin, hydrazine, sodium borohydride, formic acid, or another such reducing agent prior to the above-mentioned heat treatment in order to further promote compounding with the gold.

Method B

The above-mentioned method B involves loading the second element on the carrier, and then supporting the gold. There are no restrictions on the how the second element is supported, but the same methods as discussed for (A) above can be used, for example. Specifically, the second element is supported on the carrier by the same method as in (A) above. The second element raw material, supporting conditions, and so forth are also the same as those listed above for (A).

In some cases, though, the second element can be securely fixed to the carrier by calcing at about 300 to 900° C. under an oxidative atmosphere (in the presence of a gas containing oxygen or air) as a subsequent additional treatment that is favorable in terms of the gold support operation.

The supporting of gold on the second element-containing carrier prepared as above can be accomplished by the same method as in (A) above. In other words, the gold is supported by deposition-precipitation or other such method, after which drying and calcing are carried out in the same manner as in (A) above. Also, just as in (A) above, it is desirable to perform a heat treatment under the same reductive atmosphere as in (A) above in order to better compound the gold with the second element. If needed, this can be further combined with a reduction treatment in which a reducing agent is used.

Method C

The above-mentioned method C involves supporting the gold and the second element on the carrier at the same time. There are no restrictions on this method as long as the two components can be supported. For example, conventional method such as coprecipitation, deposition-precipitation, impregnation, or vapor phase deposition can be used. In any case, the two components can be supported simultaneously by causing a compound that includes the second element to coexist in the system in the course of supporting the gold on the carrier. Furthermore, the catalyst of the present invention, in which ultrafine metal particles including gold and a second element are supported on a carrier can be obtained by subjecting the carrier loaded with both components to a heat treatment and/or reduction treatment in the same manner as in method A or B above.

Deposition-precipitation or impregnation can be used to advantage in the present invention. With a deposition-precipitation method, it is preferable to control the conditions so that a compound including the second element will form a precipitate under conditions conducive to the precipitation of a compound (such as a hydroxide) including gold. (If the above-mentioned compound is a hydroxide, for instance, the temperature is 30 to 100° C., the pH is 5 to 10, and the gold concentration is 0.1 to 100 mmol/L.) In this case, it is preferable to use a water-soluble compound including the second element as the starting raw material, and to form a precipitate as a hydroxide including the second element from an aqueous solution of this compound. It is preferable here for a hydroxide of gold and a hydroxide of the second element to form precipitates simultaneously, and to produce a hydroxide containing both gold and the second element. The catalyst of the present invention can be obtained by further subjecting these precipitates to heat treatment and/or reduction treatment.

With an impregnation method, the catalyst of the present invention can be obtained by adding a carrier to a solution obtained by dissolving a gold compound and a compound including a second element in an organic solvent, and if necessary distilling off or otherwise removing the organic solvent, thereby causing the gold compound and the compound including the second element to adhere simultaneously to the carrier, and then performing heat treatment and/or reduction treatment. As a typical example, the catalyst of the present invention in which ultrafine gold alloy particles containing gold and a second element (such as ultrafine Au—Ni alloy particles) are supported on a carrier can be obtained by impregnating a carrier with a methanol solution containing an acetylacetonate compound of gold (such as dimethyl gold acetylacetonate) and an acetylacetonate compound of a second element (such as nickel acetylacetonate), distilling off the methanol, then drying and performing a reduction treatment.

The raw material compound used in the above-mentioned deposition-precipitation, impregnation, or other method can be the same as those disclosed in 1) or 2) above.

The catalyst of the present invention can be used to advantage in the manufacture of carboxylic esters. More specifically, this catalyst can be used in a) a reaction for preparing a carboxylic ester by reacting oxygen, an aldehyde, and an alcohol, or b) a reaction for preparing a carboxylic ester by reacting oxygen and one or more types of alcohol.

In reaction a) above, this catalyst can be applied favorably when methyl methacrylate is produced by using methacrolein and methanol, or when methyl glyoxylate is produced by using glyoxal and methanol, for example.

In reaction b) above, this catalyst can be applied favorably when methyl methacrylate is produced by using methallyl alcohol and methanol, or when methyl glycolate is manufactured by using ethylene glycol and methanol, for example.

In particular, with respect to a catalyst comprising the particles of the present invention supported on a silica carrier or a carrier containing silica, the catalyst surface may be subjected to an organic silylation treatment. This treatment enhances catalyst performance, extends catalyst life and so on. A known method can be employed for the organic silylation treatment itself, and can be carried out by a vapor phase or liquid phase process with using silylation agents such as methoxytrimethylsilane, trimethylsilyl chloride, hexamethyldisilazane, or the like.

2. Method for Producing Carboxylic Esters

The method of the present invention for producing a carboxylic ester includes 1) a method for producing a carboxylic ester by reacting an aldehyde with an alcohol in the presence of oxygen (first method), and 2) a method for producing a carboxylic ester by reacting one or more types of alcohol with oxygen (second method).

(1) First Method

The first method can be used favorably to manufacture a carboxylic ester by reacting oxygen, an aldehyde, and an alcohol in the presence of the catalyst of the present invention.

Examples of the above-mentioned aldehyde include formaldehyde, acetaldehyde, propionaldehyde, isobutylaldehyde, glyoxal, pyruvic aldehyde, and other such aliphatic aldehydes with 1 to 10 carbons; acrolein, methacrolein, crotonaldehyde, and other such $\alpha,\beta$-unsaturated aldehydes with 3 to 10 carbons; benzaldehyde, glyoxal, p-methoxybenzaldehyde, tolualdehyde, phthalaldehyde and other such aromatic aldehydes with 6 to 20 carbons; and derivatives of these aldehydes. The use of aliphatic aldehydes, $\alpha,\beta$-unsaturated aldehydes, and so forth is preferred. One or more types of these aldehydes can be used.

Examples of the above-mentioned alcohol include methanol, ethanol, isopropanol, octanol, and other such aliphatic alcohols with 1 to 10 carbons; ethylene glycol, butanediol, and other such diols with 2 to 10 carbons; allyl alcohol, methallyl alcohol, and other such aliphatic unsaturated alcohols with 3 to 10 carbons; and benzyl alcohol and other such aromatic alcohols. The use of aliphatic alcohols with 1 to 10 carbons is preferred. One or more types of these alcohols can be used.

With the manufacturing method of the present invention, the above-mentioned aldehyde and alcohol may be appropriately selected as dictated by the type of carboxylic ester desired and other such factors. For instance, if methyl methacrylate is to be prepared, methacrolein can be used as the aldehyde and methanol can be used as the alcohol.

There are no particular restrictions on the reaction proportions of the aldehyde and alcohol, but a molar ratio (aldehyde/alcohol) of about 10-1/200 is favorable, and a range of 1/2 to 1/50 is particularly good. The above range allows a carboxylic ester to be manufactured more efficiently.

With the present invention, the reaction between the aldehyde and alcohol is conducted in the presence of oxygen (molecular oxygen) and a catalyst composed of the composition of the present invention.

The above reaction may be a liquid phase reaction, vapor phase reaction, etc. The oxygen (oxygen gas) may be diluted with an inert gas such as nitrogen, argon, helium, or carbon dioxide. A gas containing oxygen such as air, can also be used for this oxygen. There are no particular restrictions on the method for supplying the oxygen to the reaction system, and any known method can be employed, but bubbling into a liquid is particularly a favorable method.

The above reaction may be conducted by continuous, batch, or semi-batch process, with no particular restrictions thereon. If the reaction format is batch, then the catalyst may be supplied all at once along with the raw materials to the reaction apparatus. If a continuous reaction format is employed, then the reaction apparatus may be packed with the catalyst ahead of time, or the catalyst may be continuously supplied along with the raw materials to the reaction apparatus. The catalyst may be in the form of a fixed bed, fluidized bed, suspended bed, or the like.

The amount of the catalyst may be appropriately determined according to the combination of aldehyde and alcohol, the type of catalyst (composition, etc.), reaction conditions, and so forth. There are no particular restrictions on the reaction time, which varies with the set conditions, but the reaction time or residence time (amount of liquid in the reaction apparatus/amount of liquid supplied) usually may be about 0.5 to 20 hours.

The conditions such as reaction temperature and pressure may all be appropriately determined according to the combination of aldehyde and alcohol, the type of catalyst, and so forth. The reaction temperature is usually about 0 to 180° C., and preferably 20 to 150° C. Setting the temperature within this range allows the reaction to proceed more efficiently. The reaction may be conducted under reduced pressure, normal pressure, or elevated pressure, but a pressure range of 0.05 to 5 MPa (gauge pressure), and particularly 0.1 to 2 MPa, can be used to advantage. The pH of the reaction system may be about 6 to 9 from the standpoint of minimizing by-products and so forth. An alkali metal compound or alkaline earth metal compound (carboxylate) can be added to the reaction system as an additive for adjusting the pH, for example.

After the above reaction, the catalyst is separated from the reaction system, and then the produced carboxylic ester may be recovered by some known separation and refining means. The separation of the catalyst may be accomplished with a known method. For instance, if the reaction system consists of the catalyst (solid) and the reaction product (liquid), then the catalyst and the reaction product can be separated by using a known solid-liquid separation method such as filtration or centrifugation.

The carboxylic ester obtained with the manufacturing method of the present invention can be used in the same applications as carboxylic esters obtained by prior art. For example, acrylic esters, methacrylic esters, and other such carboxylic esters are useful as a polymerization monomer that serves as a raw material for various kinds of acrylic resin.

(2) Second Method

The second method can be used favorably to manufacture a carboxylic ester by reacting oxygen with one or more types of alcohol in the presence of the catalyst of the present invention.

There are no particular restrictions on the above-mentioned alcohol, as long as it gives a carboxylic ester through reaction with oxygen, and alcohols that have been used as raw materials in the manufacture of carboxylic esters by known methods can be used. The alcohol may be either monohydric or polyhydric. It is preferable for the alcohol to be a primary alcohol. A polyhydric alcohol may contain a secondary alcohol in its molecule as long as it also contains at least one primary alcohol in its molecule. Specifically, it is preferable for a polyhydric alcohol to contain at least one primary alcohol in its molecule. Examples of these alcohols include methanol, ethanol, n-propanol, octanol, and other such aliphatic alcohols with 1 to 10 carbons; 1,2-ethanediol, 1,2-propanediol, 1,3-propanediol, 1,3-butanediol, 1,4-butanediol, neopentyl glycol, glycerol, 1,1,1-trimethylolpropane, pentaerythritol, erythritol, sorbitol, and other such polyhydric alcohols with 2 to 10 carbons; diethylene glycol, triethylene glycol, and other such alcohols with 2 to 10 carbons having an ether bond in their molecule; allyl alcohol, methallyl alcohol, and other such aliphatic unsaturated alcohols with 3 to 10 carbons; and benzyl alcohol and other such aromatic alcohols. One or more types of these alcohols can be used. The use of a polyhydric alcohol with 2 to 10 carbons is preferred, and the use of at least ethylene glycol or 1,2-propylene glycol is particularly favorable.

The desired carboxylic ester can be obtained with the manufacturing method of the present invention by specifying the type of alcohol used as a raw material. Specifically, the alcohol may be appropriately determined according to the type of carboxylic ester desired and other factors. For instance, a) when ethyl acetate is to be manufactured, ethanol can be used as the raw material, b) ethylene glycol can be used when 2-hydroxyethyl glycolate is manufactured, c) diethylene glycol when 1,4-dioxan-2-one is manufactured, d) ethylene glycol and methanol when methyl glycolate is manufactured, and e) 1,2-propylene glycol and methanol when methyl pyruvate and methyl lactate (mixture) are manufactured.

The amounts in which the various alcohols are used in the event that two or more types of alcohol are used may be appropriately determined according to the reaction in question. For instance, when methyl glycolate is to be manufactured by reacting oxygen with ethylene glycol and methanol, the ethylene glycol and methanol may be used in a molar ratio of 1:1.

The way in which the catalyst of the present invention is used, the reaction conditions, the refining method, and so forth can be the same as those mentioned above for the first method. The obtained carboxylic ester can also be used in a variety of applications, just as with the first method.

In particular, because the catalyst of the present invention comprises 1) ultrafine gold particles and/or 2) ultrafine metal particles containing gold and a second element other than gold, having an average particle diameter of no more than 6 nm, supported on a carrier, this catalyst exhibits better activity than in the past when used in the manufacture of a carboxylic ester. Furthermore, this performance is not readily deactivated after repeated catalyst use, as was the case with prior art, which means that a relatively high level of activity can be maintained.

BEST MODE FOR CARRYING OUT THE INVENTION

Examples and comparative examples will now be given to further clarify the characteristics of the present invention. The scope of the present invention, though, is not limited to or by these examples.

The measurement of properties and so on in the examples and comparative examples was conducted by the following methods.

(1) Amount of Ultrafine Gold Particles or Ultrafine Metal Particles Carried

This was measured by fluorescent X-ray analysis.

(2) Average Diameter of Ultrafine Gold Particles or Ultrafine Metal Particles

The particle size was examined with a transmission electron microscope (TEM) (model "HF-2000", made by Hitachi; accelerating voltage 200 kV), and the components of the particles were analyzed with an attached X-ray analyzer.

(3) Quantification Analysis of Reaction Product

The components of the reaction product in the reaction solution were quantitatively analyzed by gas chromatography and/or liquid chromatography.

(4) Conversion, Selectivity, and Yield

Conversion, selectivity, and yield were calculated from the respective equations given below.

Conversion (%)=$(1-B/A)\times 100$

Selectivity (%)=$\{C/(A-B)\}\times 100$

Yield (%)=$(C/A)\times 100$ (In the three equations above, A is the number of moles of aldehyde or alcohol supplied, B is the number of moles of remaining aldehyde or remaining alcohol, and C is the number of moles of consumed aldehyde or alcohol according to the number of moles of carboxylic ester produced.)

EXAMPLE 1-1

(1) Preparation of Catalyst 500 mL of a chloroauric acid aqueous solution with a concentration of 10 mmol/L was kept at 65 to 70° C. while being adjusted to a pH of 7 with a 0.5 N sodium hydroxide aqueous solution. 40 g of commercially available γ-alumina (trade name "AC-12R," made by Sumitomo Chemical) was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 300° C. in air, which gave a gold-loading carrier in which gold was supported on an alumina carrier (Au/γ-alumina). The amount of gold supported here was measured and found to be 4.6 wt % with respect to the carrier. The gold particle diameter here was also examined, which revealed that almost all of the gold was highly dispersed in the form of particles having a diameter of 5 nm or less, that the particle size distribution was narrow, with a peak in the range of a particle diameter of 2 to 3 nm, and that the average particle diameter was not more than 5 nm.

(2) Preparation of Carboxylic Ester

A carboxylic ester was produced using the gold-loading carrier obtained in (1) above as a catalyst.

1.5 mL of methacrolein, 15 mL of methanol, and 0.5 g of the above-mentioned gold-loading carrier were sealed in a 100 mL autoclave equipped with a rotary agitator. The interior of the system was then pressurized to 0.2 MPa with oxygen, after which the temperature was raised to 80° C. under stirring, and this temperature was maintained for 2 hours. The system was then cooled and the seal was broken, the catalyst was separated from the reaction liquid by filtration, and the reaction liquid was analyzed, which revealed the methacrolein conversion to be 88%, the methyl methacrylate selectivity and yield to be 85% and 75%, respectively, and the methyl methacrylate production activity per unit of catalyst weight to be 13.6 mol/h/kg-catalyst.

EXAMPLE 1-2

A gold-loading carrier (Au/γ-alumina) was prepared in the same manner as in Example 1-1, except that the calcination temperature of the gold-fixed substance was changed to 400° C. The amount of gold supported on this carrier was measured and found to be 4.6 wt % with respect to the carrier. The gold particle diameter here was also examined, which revealed that almost all of the gold was highly dispersed in the form of particles with a diameter of 5 nm or less, that the particle size distribution was narrow, with a peak in the range of a particle diameter of 2 to 3 nm, and that the average particle diameter was 5 nm or less.

This gold-loading carrier was used to produce a carboxylic ester in the same manner as in Example 1-1. The reaction solution thus produced was analyzed, which revealed the methacrolein conversion to be 85%, the methyl methacrylate selectivity and yield to be 84% and 71%, respectively, and the methyl methacrylate production activity per unit of catalyst weight to be 13.0 mol/h/kg-catalyst.

EXAMPLE 1-3

A gold-loading carrier (Au/γ-alumina) was prepared in the same manner as in Example 1-1, except that the calcination temperature of the gold-fixed substance was changed to 600° C. The amount of gold supported on this carrier was measured and found to be 4.6 wt % to the carrier. The gold particle diameter here was also examined, which revealed that most of the gold was highly dispersed in the form of particles with a diameter of 3 to 6 nm, and that the average particle diameter was 6 nm or less.

This gold-loading carrier was used to manufacture a carboxylic ester in the same manner as in Example 1-1. The reaction solution thus produced was analyzed, which revealed the methacrolein conversion to be 51%, the methyl methacrylate selectivity and yield to be 72% and 37%, respectively, and the methyl methacrylate production activity per unit of catalyst weight to be 6.7 mol/h/kg-catalyst.

COMPARATIVE EXAMPLE 1-1

A gold-loading carrier (Au/γ-alumina) was prepared in the same manner as in Example 1-1, except that the calcination temperature of the gold-fixed substance was changed to 700° C. The amount of gold supported on this carrier was measured and found to be 4.6 wt % with respect to the carrier. The gold particle diameter here was also examined, which revealed that most of the gold was in the form of particles having a diameter over 6 nm, and that the average particle diameter was over 6 nm.

This gold-loading carrier was used to manufacture a carboxylic ester in the same manner as in Example 1-1. The reaction solution thus produced was analyzed, which revealed the methacrolein conversion to be 27%, the methyl methacrylate selectivity and yield to be 52% and 14%, respectively, and the methyl methacrylate production activity per unit of catalyst weight to be 2.5 mol/h/kg-catalyst. These results confirmed that when the average particle diameter is over 6 nm, the catalytic activity is inferior to that in Examples 1 to 3.

COMPARATIVE EXAMPLE 1-2

A gold-loading carrier (Au/γ-alumina) was manufactured in the same manner as in Example 1-1, except that the calcination temperature of the gold-fixed substance was changed to 800° C. The amount of gold supported on this carrier was measured and found to be 4.6 wt % with respect to the carrier. The gold particle diameter here was also examined, which revealed that almost all of the gold was in the form of particles with a diameter over 6 nm, and that the average particle diameter was over 6 nm.

This gold-loading carrier was used to manufacture a carboxylic ester in the same manner as in Example 1-1. The reaction solution thus produced was analyzed, which revealed the methacrolein conversion to be 18%, the methyl methacrylate selectivity and yield to be 42% and 8%, respectively, and the methyl methacrylate production activity per unit of catalyst weight to be 1.4 mol/h/kg-catalyst.

EXAMPLE 1-4

(1) Preparation of Catalyst

① Preparation of Silica Carrier 10 g of a commercially available silica carrier (trade name "CARiACT Q-10," made by Fuji Silysia Chemical) was put into a 25 mL aqueous solution containing 7.03 g of aluminum nitrate nonahydrate, so that the silica carrier would be impregnated with this aqueous solution. After being impregnated with the aqueous solution, the silica carrier was dried for 12 hours at 120° C., and then calcined for 4 hours in air at 600° C. This gave an aluminum-silica carrier in which the silica included aluminum.

② Supporting Gold 250 mL of a chloroauric acid aqueous solution with a concentration of 10 mmol/L was kept at 65 to 70° C. while being adjusted to a pH of 7 with a 0.5 N sodium hydroxide aqueous solution. 10 g of the above-mentioned aluminum-silica carrier was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air, which gave a gold-loading carrier in which gold was supported on an aluminum-silica carrier (Au/Al/silica). The amount of gold supported here was measured and found to be 4.5 wt % with respect to the carrier. The aluminum content in the carrier was 4.5 wt %. The gold particle diameter here was also examined, which revealed that almost all of the gold was highly dispersed in the form of particles with a diameter of 5 nm or less, that the particle size distribution was narrow, with a peak in the range of a particle diameter of 2 to 3 nm, and that the average particle diameter was 5 nm or less.

(2) Manufacture of Carboxylic Ester 1.5 mL of methacrolein, 15 mL of methanol, and 0.5 g of the above-mentioned gold-loading carrier were sealed in a 100 mL autoclave equipped with a rotary agitator. The interior of the system was then pressurized to 0.2 MPa with oxygen, after which the temperature was raised to 80° C. under stirring, and this temperature was maintained for 2 hours. The system was then cooled and the seal was broken, the catalyst was separated from the reaction liquid by filtration, and the reaction liquid was analyzed, which revealed the methacrolein conversion to be 75%, the methyl methacrylate selectivity and yield to be 88% and 66%, respectively, and the methyl methacrylate production activity per unit of catalyst weight to be 12.0 mol/h/kg-catalyst.

EXAMPLE 1-5

A gold-loading carrier (Au/Ti/silica) in which gold was supported on a titanium-silica carrier was obtained in the same manner as in Example 1-4, except that a methanol solution containing 3.55 g of titanium tetra-n-butoxide was used in place of the aqueous solution containing 7.03 g of aluminum nitrate nonahydrate. The amount of gold supported here was measured and found to be 4.8 wt % with respect to the carrier. The titanium content in the carrier was 4.9 wt %. The gold particle diameter here was also examined, which revealed that nearly all of the gold was highly dispersed in the form of particles with a diameter of 5 nm or less, and that the average particle diameter was 5 nm or less.

This gold-loading carrier (Au/Ti/silica) was used to manufacture a carboxylic ester in the same manner as in Example 1-4. As a result, the methacrolein conversion was 71%, the methyl methacrylate selectivity and yield were 87% and 62%, respectively, and the methyl methacrylate production activity per unit of catalyst weight was 11.2 mol/h/kg-catalyst.

EXAMPLE 1-6

A gold-loading carrier (Au/Zn/silica) in which gold was supported on a zinc-silica carrier was obtained in the same manner as in Example 4, except that 2.28 g of zinc nitrate hexahydrate was used in place of the 7.03 g of aluminum nitrate nonahydrate. The amount of gold supported here was measured and found to be 4.5 wt % with respect to the carrier. The zinc content in the carrier was 5.0 wt %. The gold particle diameter here was also examined, which revealed that almost all of the gold was highly dispersed in the form of particles having a diameter of 5 nm or less, and that the average particle diameter was 5 nm or less.

This gold-loading carrier was used to produce a carboxylic ester in the same manner as in Example 1-4. As a result, the methacrolein conversion was 97%, the methyl methacrylate selectivity and yield were 91% and 88%, respectively, and the methyl methacrylate production activity per unit of catalyst weight was 16.0 mol/h/kg-catalyst.

EXAMPLE 1-7

A gold-loading carrier (Au/La/silica) in which gold was supported on a lanthanum-silica carrier was obtained in the same manner as in Example 1-4, except that 1.56 g of lanthanum nitrate hexahydrate was used in place of the 2.28 g of zinc nitrate hexahydrate. The amount of gold supported here was measured and found to be 4.8 wt % with respect to the carrier. The lanthanum content in the carrier was 5.0 wt %. The gold particle diameter here was also examined, which revealed that almost all of the gold was highly dispersed in the form of particles with a diameter of 5 nm or less, and that the average particle diameter was 5 nm or less.

This gold-loading carrier was used to produce a carboxylic ester in the same manner as in Example 1-4. As a result, the methacrolein conversion was 99%, the methyl methacrylate selectivity and yield were 92% and 91%, respectively, and the methyl methacrylate production activity per unit of catalyst weight was 16.5 mol/h/kg-catalyst.

EXAMPLE 1-8

A gold-loading carrier (Au/Ce/silica) in which gold was supported on a cerium-silica carrier was obtained in the same manner as in Example 1-1, except that 1.49 g of cerium nitrate pentahydrate was used in place of the 7.03 g of aluminum nitrate nonahydrate. The amount of gold supported here was measured and found to be 4.8 wt % to the carrier. The cerium content in the carrier was 4.9 wt %. The gold particle diameter here was also examined, which revealed that almost all of the gold was highly dispersed in the form of particles with a diameter of 5 nm or less, and that the average particle diameter was 5 nm or less.

This gold-loading carrier was used to manufacture a carboxylic ester in the same manner as in Example 1-4. As a result, the methacrolein conversion was 64%, the methyl methacrylate selectivity and yield were 87% and 56%, respectively, and the methyl methacrylate production activity per unit of catalyst weight was 10.1 mol/h/kg-catalyst.

EXAMPLE 1-9

A gold-loading carrier (Au/Pb—Mg/silica) in which gold was supported on a lead-magnesium/silica carrier was obtained in the same manner as in Example 1-4, except that 0.92 g of lead acetate trihydrate and 1.76 g of magnesium acetate tetrahydrate were used instead of the 7.03 g of aluminum nitrate nonahydrate. The amount of gold supported here was measured and found to be 4.8 wt % with respect to the carrier. The lead and magnesium contents in the carrier were 5.0 wt % and 2.0 wt %, respectively. The gold particle diameter here was also examined, which revealed that almost all of the gold was highly dispersed in the form of particles with a diameter of 5 nm or less, and that the average particle diameter was 5 nm or less.

This gold-loading carrier was used to prepare a carboxylic ester in the same manner as in Example 1-4. As a result, the methacrolein conversion was 83%, the methyl methacrylate selectivity and yield were 92% and 81%, respectively, and the methyl methacrylate production activity per unit of catalyst weight was 13.9 mol/h/kg-catalyst.

EXAMPLE 1-10

A gold-loading carrier (Au/La/silica) in which gold was supported on a lanthanum-silica carrier was obtained in the same manner as in Example 1-7, except that the 1.56 g of lanthanum nitrate hexahydrate was changed to 3.12 g, and the amount of the lanthanum-silica was changed from 10 g to 5 g. The amount of gold supported here was measured and found to be 8.4 wt % with respect to the carrier. The lanthanum content in the carrier was 10.1 wt %. The gold particle diameter here was also examined, which revealed that almost all of the gold was highly dispersed in the form of particles with a diameter of 5 nm or less, and that the average particle diameter was 5 nm or less.

This gold-loading carrier was used to prepare a carboxylic ester in the same manner as in Example 1-4, except that the oxygen pressure inside the system was changed to 0.3 MPa and the reaction time to 1 hour. As a result, the methacrolein conversion was 98%, the methyl methacrylate selectivity and yield were 93% and 91%, respectively, and the methyl methacrylate production activity per unit of catalyst weight was 33.0 mol/h/kg-catalyst.

EXAMPLE 1-11

Using the gold-loading carrier obtained in Example 1-10 as a catalyst, a carboxylic ester was produced in the same manner as in Example 1-10, except that the amounts of methacrolein and methanol were changed to 3.0 mL and 12 mL, respectively. As a result, the methacrolein conversion was 78%, the methyl methacrylate selectivity and yield were 89% and 69%, respectively, and the methyl methacrylate production activity per unit of catalyst weight was 50.4 mol/h/kg-catalyst.

EXAMPLE 1-12

A carboxylic ester was produced in the same manner as in Example 1-10, except that the gold-loading carrier obtained in Example 1-10 was used as the catalyst, and the amounts of methacrolein and methanol were changed to 4.0 mL and 12 mL, respectively. As a result, the methacrolein conversion was 54%, the methyl methacrylate selectivity and yield were 86% and 46%, respectively, and the methyl methacrylate production activity per unit of catalyst weight was 45.0 mol/h/kg-catalyst.

EXAMPLE 1-13

A carboxylic ester was produced using the gold-loading carrier obtained in Example 1-10. 1.5 mL of acrolein, 15 mL of methanol, and 0.5 g of the above-mentioned gold-loading carrier were sealed in a 100 mL autoclave equipped with a rotary agitator. The interior of the system was then pressurized to 0.3 MPa with oxygen, after which the temperature was raised to 70° C. under stirring, and this temperature was maintained for 3 hours. After the reaction, the reaction solution was analyzed, which revealed the acrolein conversion to be 95%, and the methyl methacrylate selectivity and yield to be 84% and 80%, respectively.

EXAMPLE 1-14

A carboxylic ester was manufactured using the gold-loading carrier obtained in Example 1-10. 2 g of a 40% glyoxal aqueous solution, 15 mL of methanol, and 0.5 g of the above-mentioned gold-loading carrier were sealed in a 100 mL autoclave equipped with a rotary agitator. The interior of the system was then pressurized to 0.3 MPa with oxygen, after which the temperature was raised to 80° C. under stirring, and this temperature was maintained for 1 hour. After the reaction, the reaction solution was analyzed, which revealed the glyoxal conversion to be 53%, and the methyl glyoxylate selectivity and yield to be 87% and 46%, respectively.

EXAMPLE 1-15

A glass tube with an inside diameter of 10 mm was packed with the gold-loading carrier obtained in Example 1-10 (used as a catalyst), and helium gas containing approximately 8 vol % methoxytrimethylsilane was made to flow through the tube at a flux of 6 L/hour in a state in which the catalyst layer temperature had been raised to 280° C. A reaction was conducted in the same manner as in Example 1-14 using 0.5 g of the silylated gold-loading carrier thus obtained as a catalyst. The resultant liquid thus obtained was analyzed, which revealed the glyoxal conversion to be 75%, and the methyl glyoxylate selectivity and yield to be 82% and 62%, respectively.

EXAMPLE 1-16

A carboxylic ester was prepared using the gold-loading carrier obtained in Example 1-10. 2 g of propionaldehyde, 15 mL of ethanol, and 0.5 g of the above-mentioned gold-loading carrier were sealed in a 100 mL autoclave equipped with a rotary agitator. The interior of the system was then pressurized to 0.3 MPa with oxygen, after which the temperature was raised to 80° C. under stirring, and this temperature was maintained for 2 hours. After the reaction, the reaction solution was analyzed, which revealed the propionaldehyde conversion to be 83%, and the ethyl propionate selectivity and yield to be 90% and 75%, respectively.

EXAMPLE 1-17

A carboxylic ester was prepared using the gold-loading carrier obtained in Example 1-10. 2 g of isobutylaldehyde, 15 mL of ethanol, and 0.5 g of the above-mentioned gold-loading carrier were sealed in a 100 mL autoclave equipped with a rotary agitator. The interior of the system was then pressurized to 0.3 MPa with oxygen, after which the temperature was raised to 65° C. under stirring, and this temperature was maintained for 2 hours. After the reaction, the reaction solution was analyzed, which revealed the isobutylaldehyde conversion to be 80%, and the ethyl isobutyrate selectivity and yield to be 88% and 70%, respectively.

EXAMPLE 1-18

A carboxylic ester was manufactured using the gold-loading carrier obtained in Example 1-10. 2 g of benzaldehyde, 15 mL of 1-propanol, and 0.5 g of the above-mentioned gold-loading carrier were sealed in a 100 mL autoclave equipped with a rotary agitator. The interior of the system was then pressurized to 0.3 MPa with oxygen, after which the temperature was raised to 70° C. under stirring, and this temperature was maintained for 4 hours. After the reaction, the reaction solution was analyzed, which revealed the benzaldehyde conversion to be 89%, and the propyl benzoate selectivity and yield to be 88% and 70%, respectively.

EXAMPLE 1-19

(1) Preparation of Catalyst 500 mL of a chloroauric acid aqueous solution with a concentration of 10 mmol/L was kept at 65 to 70° C. while being adjusted to a pH of 7 with a 0.5 N sodium hydroxide aqueous solution. 10 g of commercially available titania (anatase, made by Norton) was poured into this aqueous solution under stirring, and the stirring was continued for another hour while the system was kept at 65 to 70° C. and the pH at 7 to 8. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air, which gave a gold-loading carrier in which gold was supported on a titania carrier (Au/titania). The amount of gold supported here was measured and found to be 4.7 wt % with respect to the carrier. The gold particle diameter here was also examined, which revealed that almost all of the gold was highly dispersed in the form of particles with a diameter of 5 nm or less, and that the average particle diameter was 5 nm or less.

(2) Manufacture of Carboxylic Ester 1.5 mL of methacrolein, 15 mL of methanol, and 0.5 g of the above-mentioned gold-loading carrier were sealed in a 100 mL autoclave equipped with a rotary agitator. The interior of the system was then pressurized to 0.2 MPa with oxygen, after which the temperature was raised to 80° C. under stirring, and this temperature was maintained for 2 hours. The system was then cooled and the seal broken, the catalyst was separated from the reaction solution by filtration, and the reaction solution was analyzed, which revealed the methacrolein conversion to be 83%, the methyl methacrylate selectivity and yield to be 81% and 67%, respectively, and the methyl methacrylate production activity per unit of catalyst weight to be 12.2 mol/h/kg-catalyst.

EXAMPLE 1-20

A gold-loading carrier (Au/zirconia) was produced in the same manner as in Example 1-19, except that commercially available zirconia (made by Norton) was used in place of titania as the carrier. The amount of gold supported on this carrier was measured and found to be 4.4 wt % with respect to the carrier. The gold particle diameter here was also examined, which revealed that nearly all of the gold was highly dispersed in the form of particles with a diameter of 5 nm or less, and that the average particle diameter was 5 nm or less.

This gold-loading carrier was used to produce a carboxylic ester in the same manner as in Example 1-19. After the reaction, the reaction solution thus obtained was analyzed, which revealed the methacrolein conversion to be 69%, the methyl methacrylate selectivity and yield to be 83% and 53%, respectively, and the methyl methacrylate production activity per unit of catalyst weight to be 9.6 mol/h/kg-catalyst.

EXAMPLE 1-21

(1) Preparation of Catalyst 500 mL of an aqueous solution that contained 40.4 g of iron nitrate nonahydrate and 0.88 g of chloroauric acid tetrahydrate and that had been heated to 70° C. was poured, in its entirety, under stirring and over a period of about 1 minute, into 500 mL of an aqueous solution that contained 19.6 g of sodium carbonate and that had been heated to between 65 and 70° C. The stirring was then continued while the temperature was held between 65 and 70° C., after which the supernatant was removed by centrifugation. Stirring, washing, and drying operations using 1 L of ion exchange water were repeated three times for 10 minutes each, after which the solids thus obtained were dried for 12 hours at 120° C., and then calcined for 4 hours at 450° C. in air, which gave a gold-loading carrier in which gold was supported on iron oxide (Au/$Fe_2O_3$). The amount of gold supported here was measured and found to be 4.8 wt % with respect to the carrier. The gold particle diameter here was also examined, which revealed that almost all of the gold was highly dispersed in the form of particles with a diameter of 5 nm or less, and that the average particle diameter was 5 nm or less.

(2) Manufacture of Carboxylic Ester 1.5 mL of methacrolein, 15 mL of methanol, and 0.5 g of the above-mentioned gold-loading carrier were sealed in a 100 mL autoclave equipped with a rotary agitator. The interior of the system was then pressurized to 0.2 MPa with oxygen, after which the temperature was raised to 80° C. under stirring, and this temperature was maintained for 2 hours. The system was then cooled and the seal broken, the catalyst was separated from the reaction solution by filtration, and the reaction solution was analyzed, which revealed the methacrolein conversion to be 66%, the methyl methacrylate selectivity and yield to be 87% and 57%, respectively, and the methyl methacrylate production activity per unit of catalyst weight to be 10.3 mol/h/kg-catalyst.

EXAMPLE 1-22

A gold-loading carrier (Au/ZnO) in which gold was supported on zinc oxide was obtained in the same manner as in Example 1-21, except that 29.8 g of zinc nitrate hexahydrate was used in place of the 40.4 g of iron nitrate nonahydrate, the amount of chloroauric acid tetrahydrate was changed from 0.88 g to 0.51 g, and the amount of sodium carbonate was changed from 19.6 g to 13.2 g. The amount of gold supported here was measured and found to be 2.9 wt % with respect to the carrier. The gold particle diameter here was also examined, which revealed that almost all of the gold was highly dispersed in the form of particles with a diameter of 5 nm or less, and that the average particle diameter was 5 nm or less.

This gold-loading carrier was used as a catalyst to prepare a carboxylic ester in the same manner as in Example 1-21. After the reaction, the reaction solution was analyzed. As a result, the methacrolein conversion was 74%, the methyl methacrylate selectivity and yield were 81% and 60%, respectively, and the methyl methacrylate production activity per unit of catalyst weight was 10.9 mol/h/kg-catalyst.

EXAMPLE 2-1

(1) Preparation of Catalyst

① Supporting Gold 0.5 L of a tetrachloroauric acid aqueous solution with a concentration of 20 mmol/L was kept at 65 to 70° C. while being adjusted to a pH of 7 with a 0.5 mol/L sodium hydroxide aqueous solution. 40 g of commercially available γ-alumina (trade name "AC-12R," made by Sumitomo Chemical) was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 10 hours at 100° C., then calcined for 3 hours at 400° C. in air, which gave a gold-loading carrier in which gold was supported on γ-alumina (Au/γ-alumina). The amount of gold supported here was measured by fluorescent X-ray analysis and found to be 4.6 wt % with respect to the carrier.

② Compounding of Lead 10 g of the gold-loading carrier obtained in ① above was added to 30 mL of a methanol solution containing 0.74 g of lead acetate trihydrate, after which the methanol was distilled off at normal temperature with an evaporator to impregnate the carrier with the lead compound. A glass tube with an inside diameter of 10 mm was packed with the remaining solids, and the packing layer was heated to 450° C. while a mixed gas composed of 10% hydrogen and 90% argon was passed through for 3 hours at a flux of 6 L per hour to perform a hydrogen reduction treatment. This yielded a catalyst loading carrier (Pb—Au/γ-alumina) in which metal particles containing gold and lead were supported on an alumina carrier. The amount of lead supported here was measured and found to be 4.0 wt % with respect to the carrier. The metal particle diameter here was also examined, which revealed that all of the metal was highly dispersed in the form of particles with a diameter of 5 nm or less, that the particle size distribution was narrow, with a peak in the vicinity of a particle diameter of 2 to 3 nm, and that the average particle diameter was under 5 nm. Gold and lead components were both detected in the observed metal particles.

(2) Manufacture of Carboxylic Ester 3 mL of methacrolein, 15 mL of methanol, and 0.5 g of the above-mentioned loading carrier were sealed in a 100 mL autoclave equipped with a rotary agitator. The interior of the system was then pressurized to 0.3 MPa with oxygen, after which the temperature was raised to 80° C. under stirring, and this temperature was maintained for 1 hour. The system was then cooled and the seal was broken, the catalyst was separated from the reaction solution by filtration, and the reaction solution was analyzed, which revealed the methacrolein conversion to be 60%, the methyl methacrylate selectivity and yield to be 91% and 55%, respectively, and the methyl methacrylate production activity per unit of catalyst weight to be 39.6 mol/h/kg-catalyst.

EXAMPLE 2-2

A catalyst loading carrier in which metal particles containing gold and lead were supported on an alumina carrier was manufactured in the same manner as in (1) ② of Example 2-1, except that the amount of lead acetate trihydrate was changed from 0.74 g to 0.46 g. The gold and lead contents in the carrier were 4.6 wt % and 2.5 wt %, respectively.

This carrier was used to manufacture a carboxylic ester in the same manner as in (2) of Example 2-1. The reaction solution thus produced was analyzed, which revealed the methacrolein conversion to be 52%, the methyl methacrylate selectivity and yield to be 90% and 47%, respectively, and the methyl methacrylate production activity per unit of catalyst weight to be 33.9 mol/h/kg-catalyst.

EXAMPLE 2-3

A catalyst loading carrier in which metal particles containing gold and lead were supported on an alumina carrier was manufactured in the same manner as in (1) ② of Example 2-1, except that the amount of lead acetate trihydrate was changed from 0.74 g to 1.39 g. The gold and lead contents in the carrier were 4.6 wt % and 7.5 wt %, respectively.

This loading carrier was used to prepare a carboxylic ester in the same manner as in (2) of Example 2-1. The reaction solution thus produced was analyzed, which revealed the methacrolein conversion to be 58%, the methyl methacrylate selectivity and yield to be 88% and 51%, respectively, and the methyl methacrylate production activity per unit of catalyst weight to be 36.7 mol/h/kg-catalyst.

COMPARATIVE EXAMPLE 2-1

A lead-loading carrier (Pb/γ-alumina) was prepared using 10 g of commercially available γ-alumina (trade name "AC-12R," made by Sumitomo Chemical) instead of the 10 g of gold-loading carrier (Au/γ-alumina) used in (1)② of Example 2-1. This lead-loading carrier was used to manufacture a carboxylic ester in the same manner as in (2) of Example 2-1. After the reaction, the contents were analyzed, which revealed the methacrolein conversion to be 5%, and no methyl methacrylate was produced, so the selectivity and yield thereof were both 0%. It can be seen that no carboxylic ester whatsoever is produced with a lead-loading carrier.

EXAMPLE 2-4

(1) Preparation of Catalyst

① Supporting Lead 10 g of a commercially available silica carrier (trade name "CARiACT Q-10," made by Fuji Silysia Chemical) was put into a 25 mL aqueous solution containing 0.80 g of lead acetate trihydrate, so that the silica carrier would be impregnated with this lead compound over a warm bath. The impregnated carrier was then dried for 12 hours at 120° C., and then calcined for 4 hours at 600° C. in air. This gave a lead-silica carrier in which lead was supported on silica.

② Supporting Gold 1.0 L of a tetrachloroauric acid aqueous solution with a concentration of 10 mmol/L was kept at 65 to 70° C. while being adjusted to a pH of 7 with a 0.5 mol/L sodium hydroxide aqueous solution. 10 g of the above-mentioned lead-silica carrier was poured into this aqueous solution under stirring, and the stirring was continued for another hour while the system was kept at 65 to 70° C. The system was then allowed to stand and the supernatant was removed. 0.8 L of ion exchange water was added to the remaining goldfixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air. This was packed into a glass tube, and a mixed gas composed of 10% hydrogen and 90% argon was passed through for 6 hours at 400° C. to perform a hydrogen reduction treatment. This yielded a loading carrier (Au—Pb/silica) in which metal particles containing gold and lead were supported on a silica carrier. The amounts of gold and lead supported here were measured and found to be 4.5 wt % and 4.9 wt %, respectively, with respect to the carrier. The metal particle diameter here was also examined, which revealed that almost all of the metals was highly dispersed in the form of particles with a diameter of 5 nm or less, and that the average particle diameter was 5 nm or less. Gold and lead components were both detected in the observed metal particles.

(2) Manufacture of Carboxylic Ester 2 mL of methacrolein, 15 mL of methanol, and 0.5 g of the above-mentioned loading carrier were sealed in a 100 mL autoclave equipped with a rotary agitator. The interior of the system was then pressurized to 0.2 MPa with oxygen, after which the temperature was raised to 80° C. under stirring, and this temperature was maintained for 2 hours. The system was then cooled and the seal was broken, the loading carrier was separated from the reaction solution by filtration, and the reaction solution was analyzed, which revealed the methacrolein conversion to be 96%, the methyl methacrylate selectivity and yield to be 88% and 84%, respectively, and the methyl methacrylate production activity per unit of catalyst weight to be 20.4 mol/h/kg-catalyst.

EXAMPLE 2-5

(1) Preparation of Catalyst

① Supporting Lead 10 g of a commercially available silica carrier (trade name "CARiACT Q-15," made by Fuji Silysia Chemical) was put into a 25 mL aqueous solution containing 7.03 g of aluminum acetate nonahydrate, so that the silica carrier would be impregnated with this aluminum compound over a warm bath. The impregnated carrier was then dried for 12 hours at 120° C., and then calcined for 4 hours at 600° C. in air. This gave an aluminum-silica carrier in which lead was supported on silica.

② Supporting Gold 250 mL of a tetrachloroauric acid aqueous solution with a concentration of 10 mmol/L was kept at 65 to 70° C. while being adjusted to a pH of 7 with a 0.5 mol/L potassium hydroxide aqueous solution. 10 g of the above-mentioned aluminum-silica carrier was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air. After this, 25 mL of a methanol solution containing 0.93 g of lead acetate trihydrate was added, and the methanol was distilled off under normal pressure, which gave a loading carrier in which a lead compound was supported. This was packed into a glass tube, and nitrogen gas containing 10 to 20% methanol vapor was passed through for 4 hours at 400° C. at a flux of approximately 7.5 L/hour. This yielded a loading carrier (Pb—Au/Al/silica) in which metal particles containing gold and lead were supported on an aluminum-silica carrier. The amounts of gold and lead supported here were measured and found to be 4.5 wt % and 5.0 wt %, respectively, with respect to the carrier. The aluminum content in the carrier (aluminum/silica) was 5.0 wt %.

The metal particle diameter here was also examined, which revealed that all of the metals was highly dispersed in the form of particles with a diameter of 5 nm or less, and that the average particle diameter was 5 nm or less. Gold and lead components were both detected in the observed metal particles.

(2) Manufacture of Carboxylic Ester 3 mL of methacrolein, 12 mL of methanol, and 0.5 g of the above-mentioned loading carrier were sealed in a 100 mL autoclave equipped with a rotary agitator. The interior of the system was then pressurized to 0.3 MPa with oxygen, after which the temperature was raised to 80° C. under stirring, and this temperature was maintained for 1 hour. The system was then cooled and the seal broken, the catalyst was separated from the reaction solution by filtration, and the reaction solution was analyzed, which revealed the methacrolein conversion to be 81%, the methyl methacrylate selectivity and yield to be 86% and 70%, respectively, and the methyl methacrylate production activity per unit of catalyst weight to be 50.7 mol/h/kg-catalyst.

EXAMPLE 2-6

Using the carrier obtained in Example 2-5 as a catalyst, a carboxylic ester was manufactured in the same manner as in Example 2-5, except that the starting materials were changed to 3 mL of methacrolein and 13 mL of methanol and that the reaction conditions were changed to maintain the temperature of 70° C. for 4 hours. The reaction solution was analyzed, which revealed the methacrolein conversion to be 98%, the methyl methacrylate selectivity and yield to be 87% and 85%, respectively, and the methyl methacrylate production activity per unit of catalyst weight to be 19.1 mol/h/kg-catalyst.

EXAMPLE 2-7

Using the carrier obtained in Example 2-5 as a catalyst, a carboxylic ester was manufactured in the same manner as in Example 2-5, except that the starting materials were changed to 2 g of a 40% glyoxal aqueous solution and 15 mL of methanol. The reaction solution was analyzed, which revealed the glyoxal conversion to be 74%, the methyl glyoxylate selectivity and yield to be 88% and 65%, respectively, and the methyl glyoxylate production activity per unit of catalyst weight to be 17.9 mol/h/kg-catalyst.

EXAMPLE 2-8

(1) Preparation of Catalyst 250 mL of a chloroauric acid aqueous solution (10 mM) containing 1.05 g of bismuth nitrate pentahydrate was heated to 60° C. under stirring. 10 g of commercially available titania (trade name "P-25," made by Nippon Aerosil) was added, after which stirring was continued for another hour while the pH was maintained between 6 and 7 with a 0.5 mol/L sodium hydroxide aqueous solution. The solids were then filtered and washed three times with 500 mL of ion exchange water. The solids thus obtained were calcined for 4 hours at 500° C. in air. This product was packed into a glass tube, after which a mixed gas of 20% hydrogen and 80% nitrogen was passed through at a flux of 6 L/hour to perform a hydrogen reduction treatment for 4 hours at 450° C. This gave a catalyst loading carrier (Au—Bi/titania) in which metal particles containing gold and bismuth were supported on a titania carrier. The amounts of gold and lead supported here were measured and found to be 4.5 wt % and 1.6 wt %, respectively, with respect to the carrier.

The metal particle diameter here was also examined, which revealed that almost all of the metals was highly dispersed in the form of particles with a diameter of 3 to 6 nm, and that the average particle diameter was 6 nm or less. Gold and bismuth components were both detected in the observed metal particles.

(2) Manufacture of Carboxylic Ester 3.0 g of benzaldehyde, 20 mL of ethanol, and 0.5 g of the above-mentioned loading carrier were sealed in a 100 mL autoclave equipped with a rotary agitator. The interior of the system was then pressurized to 0.3 MPa with oxygen, after which the temperature was raised to 90° C. under stirring, and this temperature was maintained for 4 hours. The system was then cooled and the seal broken, the catalyst was separated from the reaction solution by filtration, and the reaction solution was analyzed, which revealed the benzaldehyde conversion to be 62%, and the ethyl benzoate (a carboxylic ester) selectivity and yield to be 75% and 47%, respectively.

EXAMPLE 2-9

(1) Preparation of Catalyst

① Supporting Zinc 10 g of a commercially available silica carrier (trade name "CARiACT Q-15," made by Fuji Silysia Chemical) was put into a 25 mL aqueous solution containing 1.51 g of zinc nitrate hexahydrate, so that the silica carrier would be impregnated with this zinc compound over a warm bath. The impregnated carrier was then dried for 12 hours at 120° C., and then calcined for 4 hours at 600° C. in air. This gave a zinc-silica carrier in which zinc was supported on silica.

② Supporting Gold 200 mL of a tetrachloroauric acid aqueous solution with a concentration of 10 mmol/L was kept at 65 to 70° C. while being adjusted to a pH of 7 with a 0.5 mol/L potassium hydroxide aqueous solution. 10 g of the above-mentioned zinc-silica carrier was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 450° C. in air. This was packed into a glass tube, and a mixed gas composed of 10% hydrogen and 90% argon was used to perform a hydrogen reduction treatment for 4 hours at 500° C. in order to promote the compounding of the gold and zinc. This yielded a loading carrier (Au/Zn/silica) in which metal particles containing gold and zinc were supported on a silica carrier. The amounts of gold and zinc supported here were measured and found to be 3.2 wt % and 3.3 wt %, respectively, with respect to the carrier.

The metal particle diameter here was also examined, which revealed that almost all of the metals was highly dispersed in the form of particles with a diameter of 2 to 6 nm, and that the average particle diameter was 6 nm or less. Gold and zinc components were both detected in the observed metal particles.

(2) Manufacture of Carboxylic Ester 3 mL of isobutylaldehyde, 20 mL of ethanol, and 1.0 g of the above-mentioned loading carrier (Au/Zn/silica) were sealed in a 100 mL autoclave equipped with a rotary agitator. The interior of the system was then pressurized to 0.3 MPa with oxygen, after which the temperature was raised to 65° C. under stirring, and this temperature was maintained for 5 hours. The system was then cooled and the seal broken, the catalyst was separated from the reaction solution by filtration, and the reaction solution was analyzed, which revealed the isobutylaldehyde conversion to be 94%, and the ethyl isobutyrate selectivity and yield to be 89% and 84%, respectively.

EXAMPLE 2-10

A carboxylic ester was manufactured using the loading carrier obtained in Example 2-1 (Pb—Au/γ-alumina) as a catalyst.

3.0 mL of methacrolein, 13 mL of methanol, and 1.0 g of the above-mentioned loading carrier were sealed in a 100 mL autoclave equipped with a rotary agitator. The interior of the system was then pressurized to 0.3 MPa with oxygen, after which the temperature was raised to 80° C. under stirring, and this temperature was maintained for 1 hour. The system was then cooled and the seal broken, the catalyst was separated from the reaction solution by filtration, and the reaction solution was analyzed, which revealed the methacrolein conversion to be 83%, the methyl methacrylate selectivity and yield to be 88% and 73%, respectively, and the methyl methacrylate production activity per unit of catalyst weight to be 26.5 mol/h/kg-catalyst.

The above-mentioned filtered catalyst was then once again sealed in a 100 mL autoclave equipped with a rotary agitator along with 3.0 mL of methacrolein and 13 mL of methanol, and a second reaction was conducted in the same manner as above. The reaction was analyzed the same as before, which revealed the methacrolein conversion to be 79%, the methyl methacrylate selectivity and yield to be 86% and 68%, respectively, and the methyl methacrylate production activity per unit of catalyst weight to be 24.6 mol/h/kg-catalyst.

Third and fourth reactions were then carried out in the same way, and the reaction liquid was analyzed the same as before. The results of the third reaction were a methacrolein conversion of 81%, methacrylate selectivity and yield of 85% and 69%, and methyl methacrylate production activity per unit of catalyst weight of 25.0 mol/h/kg-catalyst. The results of the fourth reaction were a methacrolein conversion of 80%, methacrylate selectivity and yield of 86% and 69%, and methyl methacrylate production activity per unit of catalyst weight of 25.0 mol/h/kg-catalyst.

It can be seen from the above results that when the catalyst of the present invention is used as an oxidation reaction catalyst, a relatively high level of catalyst activity can be maintained, without a drop in performance after repeated reactions.

EXAMPLE 2-11

(1) Preparation of Catalyst

Methanol was added to 30.4 g of an Aldrich reagent (75 wt % propanol solution of titanium diisopropoxide bisacetylacetonate) so as to bring the total amount up to 200 mL. 50 g of a commercially available silica carrier (made by Fuji Silysia Chemical, specific surface area of 179 m$^2$/g, 100 to 500 mesh) was added to this, and as much of the solvent as possible was distilled off at 80° C. and normal pressure with an evaporator. The solids were then dried for 10 hours at 120° C., and then calcined for 4 hours at 600° C. in air. The titanium-silica carrier thus obtained was subjected to fluorescent X-ray analysis. As a result, it was confirmed that titanium was supported as TiO$_2$ in an amount of 10 wt % with respect to the silica. Gold was supported on this carried by the same operation as in Example 2-1. 2 g of the gold-loading carrier thus obtained was impregnated with 20 mL of a methanol solution containing 0.178 g of germanium (III) n-butoxide (Glest reagent). A glass tube was then packed with this product, and a hydrogen reduction treatment was conducted for 3 hours at 400° C. while a mixed gas of hydrogen and nitrogen (hydrogen:nitrogen=1:9 (volumetric ratio)) was passed through. This gave a loading carrier (Ge—Au/Ti-silica) in which metal particles containing gold and germanium were supported on a titanium-silica carrier. The amounts of gold and germanium supported here were measured and found to be 4.2 wt % and 2.0 wt %, respectively. The metal particle diameter here was also examined, which revealed that the average particle diameter was 6 nm or less, and gold and germanium components were both detected in the observed metal particles.

(2) Manufacture of Carboxylic Ester 300 g of 1-butanol was added to 60 g of a 40 wt % glyoxal aqueous solution (Wako Pure Chemical), and most of the water was distilled off as an azeotropic composition with the 1-butanol at normal pressure and 90° C. with an evaporator. This gave a butanol solution of glyoxal (containing 19.4 wt % glyoxal and 80.6 wt % butanol). 5.17 g of the above-mentioned butanol solution, 8.90 g of 1-butanol, and 0.6 g of the above-mentioned metal-loading carrier were then put into an autoclave equipped with a condenser, the system was maintained at an internal pressure of 0.5 MPa at 80° C. under stirring while a mixed gas of hydrogen and nitrogen (hydrogen:nitrogen=1:9 (volumetric ratio)) was bubbled into the solution at a flux of 500 mL/minute, and the reaction was allowed to continue for 5 hours. After the reaction, the reaction solution was analyzed, which revealed the glyoxal conversion to be 87%, and the 1-butyl glyoxylate (the product) selectivity and yield to be 73% and 64%, respectively.

EXAMPLE 2-12

(1) Preparation of Catalyst

A loading carrier in which fine particles containing gold and antimony were supported on a titanium-silica carrier (Sb—Au/Ti-silica) was obtained by the same operation as in Example 2-11, except that 0.121 g of antimony(III) n-butoxide (Glest reagent) was used in place of the germanium (III) n-butoxide. The amounts of gold and antimony supported here were measured and found to be 4.2 wt % and 2.2 wt %, respectively. The metal particle diameter here was also examined, which revealed that the average particle diameter was 6 nm or less, and gold and antimony components were both detected in the observed metal particles.

(2) Manufacture of Carboxylic Ester 5.17 g of the butanol solution of glyoxal obtained in Example 2-11, 9.62 g of 1-octanol, and 0.6 g of the above-mentioned metal-loading carrier were put into an autoclave, and an oxidation reaction was conducted by the same operation as in Example 2-11. The reaction solution thus obtained was analyzed, which revealed the glyoxal conversion to be 90%, and the combined 1-octyl glyoxylate and 1-butyl glyoxylate (the product) selectivity and yield to be 74% and 67%, respectively.

EXAMPLE 2-13

(1) Preparation of Catalyst 2 g of the titanium-silica carrier obtained in Example 2-11 was impregnated with an aqueous solution containing 0.118 g of indium acetate (III) (Aldrich catalyst). This impregnated carrier was then calcined for 4 hours at 500° C. in air, which yielded an indium-titanium-silica carrier. Gold was supported on this carried by the same operation as in Example 2-1 to obtain a gold-loading carrier. A glass tube was then packed with this loading carrier, and a hydrogen reduction treatment was conducted for 3 hours at 400° C. while a mixed gas of hydrogen and nitrogen (hydrogen:nitrogen=1:9 (volumetric ratio)) was passed through. This gave a loading carrier (In—Au/Ti-silica) in which metal particles containing gold and indium were supported on a titanium-silica carrier. The amounts of gold and indium supported here were measured and found to be 3.7 wt % and 2.3 wt %, respectively. The metal particle diameter here was also examined, which revealed that the average particle diameter was 6 nm or less, and gold and indium components were both detected in the observed metal particles.

(2) Manufacture of Carboxylic Ester

An oxidation reaction was conducted by the same operation as in Example 2-11, except that 1.7 g of methacrolein, 11.9 g of methanol, and 1 g of the above-mentioned loading carrier were put into an autoclave and the internal pressure was set at 1 MPa. The reaction solution thus obtained was analyzed, which revealed the methacrolein conversion to be 72%, and the methyl methacrylate selectivity and yield to be 89% and 64%, respectively.

EXAMPLE 2-14

(1) Preparation of Catalyst 2 g of the titanium-silica carrier obtained in Example 2-11 was impregnated with a nitric acid aqueous solution containing 1.10 g of tellurium oxide (Tokyo Kasei reagent). This impregnated carrier was then calcined for 4 hours at 500° C. in air, which gave a tellurium-titanium-silica carrier. A gold-loading carrier was obtained by supporting gold on this carrier in the same way as in Example 2-1. A glass tube was then packed with this product, and a hydrogen reduction treatment was carried out for 3 hours at 400° C. while a mixed gas of hydrogen and nitrogen (hydrogen:nitrogen=1:9 (volumetric ratio)) was passed through. This gave a catalyst loading carrier (Au—Te/Ti-silica) in which metal particles containing gold and tellurium were supported on a titanium-silica carrier. The amounts of gold and tellurium supported here were measured and found to be 4.6 wt % and 4.0 wt %, respectively. The metal particle diameter here was also examined, which revealed that the average particle diameter was under 6 nm, and gold and tellurium components were both detected in the observed metal particles.

(2) Manufacture of Carboxylic Ester 3 g of a pyruvic aldehyde aqueous solution (a 40 wt % aqueous solution made by Wako Pure Chemical), 20 g of ethanol, and 1 g of the above-mentioned loading carrier were put into an autoclave, and an oxidation reaction was conducted by the same operation as in Example 2-11. The reaction solution thus obtained was analyzed, which revealed the pyruvic aldehyde conversion to be 48%, and the ethyl pyruvate selectivity and yield to be 86% and 41%, respectively.

EXAMPLE 2-15

(1) Preparation of Catalyst 250 mL of a chloroauric acid aqueous solution with a concentration of 10 mmol/L was kept at 65 to 70° C. while being adjusted to a pH of 6.2 with a 0.5 N sodium hydroxide aqueous solution. 2 g of the titanium-silica carrier obtained in Example 1-23 was added to this aqueous solution, and once the pH reached 6, 50 mL of an aqueous solution containing 0.21 g of nickel(II) acetate tetrahydrate (made by Wako Pure Chemical) was added. Stirring was then continued for an hour while the system was kept at 70° C. and a pH of 6.2. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 120° C., after which the above-mentioned solids were packed in a glass tube, and a hydrogen reduction treatment was conducted for 3 hours at 400° C. while a mixed gas of hydrogen and nitrogen (hydrogen:nitrogen=1:9 (volumetric ratio)) was passed through. This gave a loading carrier (Au—Ni/Ti-silica) in which metal particles containing gold and nickel were supported on a titanium-silica carrier. The amounts of gold and nickel supported here were measured and found to be 4.0 wt % and 2.4 wt %, respectively. The metal particle diameter here was also examined, which revealed that the average particle diameter was 6 nm or less, and gold and nickel components were both detected in the observed metal particles.

(2) Manufacture of Carboxylic Ester

An oxidation reaction was conducted by the same operation as in Example 2-11, except that the above-mentioned carrier was used as the catalyst. The reaction solution thus obtained was analyzed, which revealed the glyoxal conversion to be 94%, and the 1-butyl glyoxylate (the product) selectivity and yield to be 75% and 71%, respectively.

EXAMPLE 2-16

(1) Preparation of Catalyst

A loading carrier in which metal particles containing gold and cobalt were supported on a titanium-silica carrier was obtained in the same manner as in Example 2-15, except that 0.22 g of cobalt acetate tetrahydrate (made by Wako Pure Chemical) was used in place of the nickel acetate. The amounts of gold and cobalt supported here were measured and found to be 4.1 wt % and 2.6 wt %, respectively. The metal particle diameter here was also examined, which revealed that the average particle diameter was 6 nm or less, and gold and cobalt components were both detected in the observed metal particles.

(2) Manufacture of Carboxylic Ester

An oxidation reaction was conducted by the same operation as in Example 2-11, except that 4 g of pyruvic aldehyde (40 wt % aqueous solution made by Wako Pure Chemical), 20 g of methanol, and 1 g of the above-mentioned loading carrier were put in the autoclave. The reaction solution thus obtained was analyzed, which revealed the pyruvic aldehyde conversion to be 55%, and the methyl pyruvate (the product) selectivity and yield to be 81% and 45%, respectively.

EXAMPLE 2-17

(1) Preparation of Catalyst 5 g of aluminum-silica (silica carrier containing 5 wt % aluminum, trade name "CARiACT Q-30," made by Fuji Silysia Chemical) was added to 25 mL of a methanol solution containing 0.32 g of dimethyl gold acetylacetonate and 1.26 g of iron(III) acetylacetonate. The methanol was distilled off at 40° C. and normal pressure with an evaporator. The residue was dried in air for 12 hours at 100° C., after which it was calcined in air for 3 hours at 300° C. This product was packed into a glass tube, and a hydrogen reduction treatment was conducted for 3 hours at 450° C. while a mixed gas of hydrogen and nitrogen (hydrogen:nitrogen=1:9 (volumetric ratio)) was passed through. This gave a catalyst loading carrier (Au—Fe/Al-silica) in which metal particles containing gold and iron were supported on an aluminum-silica carrier. The amounts of gold and iron supported here were measured and found to be 4.0 wt % and 4.1 wt %, respectively. The metal particle diameter here was also examined, which revealed that almost all of the metals was highly dispersed in the form of particles with a diameter of 6 nm or less, and that the average particle diameter was under 6 nm. Gold and iron components were both detected in the observed metal particles.

(2) Manufacture of Carboxylic Ester

A carboxylic ester was manufactured using the loading carrier obtained in (1) above (Au—Fe/Al-silica) as a catalyst. 3 mL of methacrolein, 15 mL of methanol, and 1 g of the above-mentioned loading carrier were sealed in a 100 mL autoclave equipped with a rotary agitator. The interior of the system was then pressurized to 0.5 MPa with oxygen and to 0.3 MPa with nitrogen, after which the temperature was raised to 80° C. under stirring, and this temperature was maintained for 2 hours. After the reaction, the obtained reaction solution was analyzed, which revealed the methacrolein conversion to be 72%, and the methyl methacrylate selectivity and yield to be 85% and 61%, respectively.

EXAMPLE 3-1

(1) Preparation of Catalyst

① Supporting Gold 0.5 L of a tetrachloroauric acid aqueous solution with a concentration of 20 mmol/L was kept at 65 to 70° C. while being adjusted to a pH of 7 with a 0.5 N sodium hydroxide aqueous solution. 40 g of commercially available γ-alumina (trade name "Neobead," made by Mizusawa Chemical) was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air, which gave a catalyst loading carrier (Au/yalumina) in which gold was supported on an alumina carrier.

② Compounding of Lead 10 g of the gold-loading carrier was added to 30 mL of a methanol solution containing 0.74 g of lead acetate trihydrate, after which the methanol was distilled off under normal pressure with an evaporator. A glass tube with an inside diameter of 10 mm was packed with the remaining fixed material, and the packing layer was heated to 350° C. while a mixed gas composed of 10% hydrogen and 90% argon was passed through for 6 hours at a flux of 6 L per hour to perform a hydrogen reduction treatment. This yielded a loading carrier (Pb—Au/γ-alumina) in which metal fines containing gold and lead were supported on an alumina carrier.

The amounts of gold and lead supported here were measured and found to be 4.6 wt % and 4.0 wt %, respectively, with respect to the carrier. The metal particle diameter here was also examined, which revealed that nearly all of the metal was highly dispersed in the form of particles with a diameter of 5 nm or less, that the particle size distribution was narrow, with a peak in the vicinity of a particle diameter of 2 to 3 nm, and that the average particle diameter was 5 nm or less. Gold and lead components were both detected in the observed metal particles.

(2) Manufacture of Carboxylic Ester 3 g of methallyl alcohol, 24 g of methanol, and 1 g of the above-mentioned loading carrier were sealed in a 100 mL autoclave equipped with a rotary agitator. The interior of the system was then pressurized to 0.3 MPa with oxygen, after which the temperature was raised to 90° C. under stirring, and this temperature was maintained for 3 hours. During this time the supply of oxygen was continued so as to maintain the above-mentioned internal pressure. The system was then cooled and the seal broken, and the reaction solution was analyzed, which revealed the methallyl alcohol conversion to be 86%, and the methallyl alcohol selectivity and yield (based on the supplied methallyl alcohol) to be 81% and 70%, respectively.

EXAMPLE 3-2

A carboxylic ester was manufactured in the same manner as in Example 1 (2), except that 3 g of methyl α-hydroxymethylacrylate was used in place of the 3 g of methallyl alcohol used in Example 3-1. As a result, the methyl α-hydroxymethylacrylate conversion was 26%, and the dimethyl methylenemalonate (the product) selectivity and yield were 88% and 23%, respectively.

EXAMPLE 3-3

A carboxylic ester was manufactured in the same manner as in Example 3-1 (2), except that 3 g of ethylene glycol was used in place of the 3 g of methallyl alcohol used in Example 3-1. As a result, the ethylene glycol conversion was 43%, and the methyl glycolate (the product) selectivity and yield (based on the supplied ethylene glycol) were 84% and 36%, respectively.

EXAMPLE 3-4

A carboxylic ester was prepared in the same manner as in Example 3-1 (2), except that 3 g of 1,3-propanediol was used in place of the 3 g of methallyl alcohol used in Example 3-1. As a result, the 1,3-propanediol conversion was 36%, and the dimethyl malonate (the product) selectivity and yield were 85% and 31%, respectively.

EXAMPLE 3-5

(1) Preparation of Catalyst

① Manufacture of Lanthanum-silica Carrier 10 g of a commercially available silica carrier (trade name "CARiACT Q-10," made by Fuji Silysia Chemical) was impregnated with a 25 mL aqueous solution containing 3.12 g of lanthanum nitrate hexahydrate over a warm bath. This product was then was dried for 120 minutes at 120° C., and then calcined for 4 hours in air at 600° C. This gave a lanthanum-silica carrier in which lanthanum was supported on a silica carrier.

② Supporting Gold 250 mL of a tetrachloroauric acid aqueous solution with a concentration of 100 mmol/L was kept at 65 to 70° C. while being adjusted to a pH of 7 with a 0.5 N sodium hydroxide aqueous solution. 5 g of the carrier was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air, which gave a loading carrier in which gold was supported on a lanthanum-silica carrier (Au/La-silica).

The amounts of gold and lanthanum supported here were measured and found to be 8.4 wt % and 10.1 wt %, respectively, with respect to the carrier. The metal particle diameter here was also examined, which revealed that almost all of the metals was highly dispersed in the form of particles with a diameter of 5 nm or less, and that the average particle diameter was 5 nm or less.

(2) Manufacture of Carboxylic Ester 15 g of ethanol and 0.5 g of the above-mentioned loading carrier were sealed in a 100 mL autoclave equipped with a rotary agitator. The interior of the system was then pressurized to 0.2 MPa with oxygen, after which the temperature was raised to 100° C. under stirring, and this temperature was maintained for 4 hours. During this time the supply of oxygen was continued so as to maintain the above-mentioned internal pressure. The system was then cooled and the seal broken, and the reaction product was analyzed, which revealed the ethanol conversion to be 18%, and the ethyl acetate (the product) selectivity and yield to be 90% and 16%, respectively.

EXAMPLE 3-6

(1) Preparation of Catalyst

① Supporting Aluminum 10 g of a commercially available silica carrier (trade name "CARiACT Q-15," made by Fuji Silysia Chemical) was impregnated with a 25 mL aqueous solution containing 7.03 g of aluminum nitrate nonahydrate over a warm bath. This product was then was dried for 12 hours at 120° C., and then calcined for 4 hours in air at 600° C. This gave an aluminum-silica carrier in which aluminum was supported on a silica carrier.

② Supporting Gold and Lead 250 mL of a tetrachloroauric acid aqueous solution with a concentration of 10 mmol/L was kept at 65 to 70° C. while being adjusted to a pH of 7 with a 0.5 mol/L potassium hydroxide aqueous solution. 10 g of the above-mentioned aluminum-silica carrier was poured into this aqueous solution under stirring, and the stirring was continued for another hour while the system was kept at 65 to 70° C. The system was then allowed to stand and the supernatant was removed. 0.8 L of ion exchange water was added to the remaining solid substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air. After this, 25 mL of a methanol solution containing 0.93 g of lead acetate trihydrate was added, and the methanol was removed with an evaporator under normal pressure, after which nitrogen gas containing 10 to 20% methanol vapor was passed through for 4 hours at 400° C. and a flux of approximately 7.5 L/hour. This gave a loading carrier in which metal particles containing gold and lead were supported on an aluminum-silica carrier (Pb—Au/Al/silica). The amounts of gold and lead supported here were measured and found to be 4.5 wt % and 5.0 wt %, respectively, with respect to the carrier. The aluminum content in this carrier (Al/silica) was 5.0 wt %. The metal particle diameter here was also examined, which revealed that almost all of the metals was highly dispersed in the form of particles with a diameter of 5 nm or less, and that the average particle diameter was 5 nm or less. Gold and lead components were both detected in the observed metal particles.

(2) Manufacture of Carboxylic Ester 1.5 g of ethylene glycol, 15 mL of dioxane, and 0.5 g of the above-mentioned loading carrier were sealed in a 100 mL autoclave equipped with a rotary agitator. The interior of the system was then pressurized to 0.3 MPa with oxygen, after which the temperature was raised to 80° C. under stirring, and this temperature was maintained for 1 hour. The system was then cooled and the seal was broken, the catalyst was separated from the reaction solution by filtration, and the reaction product was analyzed, which revealed the ethylene glycol conversion to be 25%, and the hydroxyethyl glycolate (the product) selectivity and yield (based on the supplied ethylene glycol) to be 91% and 23%, respectively.

EXAMPLE 3-7

(1) Preparation of Catalyst 250 mL of a chloroauric acid aqueous solution (10 mM) containing 1.05 g of bismuth nitrate pentahydrate was heated to 60° C. under stirring. 10 g of commercially available titania (trade name "P-25," made by Nippon Aerosil) was added, after which stirring was continued for another hour while the pH was maintained between 6 and 7 with a 0.5 mol/L sodium hydroxide aqueous solution. The solids were then filtered and washed three times with 500 mL of ion exchange water. The solids thus obtained were calcined for 4 hours at 500° C. in air. This product was packed into a glass tube, after which a mixed gas of 20% hydrogen and 80% nitrogen was passed through at a flux of 6 L/hour to perform a hydrogen reduction treatment for 4 hours at 450° C. This gave a catalyst loading carrier (Au—Bi/titania) in which metal particles containing gold and bismuth were supported on a titania carrier. The amounts of gold and bismuth supported here were measured and found to be 4.5 wt % and 1.6 wt %, respectively, with respect to the carrier. The metal particle diameter here was also examined, which revealed that almost all of the metals was highly dispersed in the form of particles with a diameter of 3 to 6 nm, and that the average particle diameter was 6 nm or less. Gold and bismuth components were both detected in the observed metal particles.

(2) Manufacture of Carboxylic Ester 1.5 g of diethylene glycol, 20 mL of diisopropyl ether, and 0.5 g of the above-mentioned carrier were sealed in a 100 mL autoclave equipped with a rotary agitator. The interior of the system was then pressurized to 0.3 MPa with oxygen, after which the temperature was raised to 90° C. under stirring, and this temperature was maintained for 4 hours. The system was then cooled and the seal broken, the catalyst was separated from the reaction solution by filtration, and the reaction solution was analyzed, which revealed the diethylene glycol conversion to be 24%, and the 1,4-dioxan-2-one (the product) selectivity and yield to be 88% and 21%, respectively.

EXAMPLE 3-8

(1) Preparation of Catalyst

① Supporting Zinc 10 g of a commercially available silica carrier (trade name "CARiACT Q-15," made by Fuji Silysia Chemical) was impregnated with a 25 mL aqueous solution containing 1.51 g of zinc nitrate hexahydrate over a warm bath. The impregnated carrier was then dried for 12 hours at 120° C., and then calcined for 4 hours at 600° C. in air. This gave a zinc-silica carrier in which zinc was supported on silica.

② Supporting Gold 200 mL of a tetrachloroauric acid aqueous solution with a concentration of 10 mmol/L was kept at 65 to 70° C. while being adjusted to a pH of 7 with a 0.5 mol/L potassium hydroxide aqueous solution. 10 g of the above-mentioned zinc-silica carrier was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 450° C. in air. This was packed into a glass tube, and a mixed gas composed of 10% hydrogen and 90% argon was used to perform a hydrogen reduction treatment for 4 hours at 500° C. in order to promote the compounding of the gold and zinc. This yielded a catalyst loading carrier (Au/Zn/silica) in which metal particles containing gold and zinc were supported on a silica carrier. The amounts of gold and zinc supported here were measured and found to be 3.2 wt % and 3.3 wt %, respectively, with respect to the carrier. The metal particle diameter here was also examined, which revealed that almost all of the metals was highly dispersed in the form of particles with a diameter of 2 to 6 nm, and that the average particle diameter was 6 nm or less. Gold and zinc components were both detected in the observed metal particles.

(2) Manufacture of Carboxylic Ester

A carboxylic ester was manufactured using the loading carrier (Au/Zn/silica) obtained in (1) above as a catalyst.

1.5 g of 1,6-hexanediol, 15 mL of toluene, and 1.0 g of the above-mentioned loading carrier were sealed in a 100 mL autoclave equipped with a rotary agitator. The interior of the system was then pressurized to 0.3 MPa with oxygen, after which the temperature was raised to 65° C. under stirring, and this temperature was maintained for 5 hours. The system was then cooled and the seal broken, the catalyst was separated from the reaction solution by filtration, and the reaction solution was analyzed, which revealed the 1,6-hexanediol conversion to be 18%, and selectivity and yield of the product, à-caprolactam to be 82% and 15%, respectively.

EXAMPLE 3-9

(1) Preparation of Catalyst 500 mL of a tetrachloroauric acid aqueous solution with a concentration of 5 mmol/L was kept at 65 to 70° C. while being adjusted to a pH of 7 with a 0.5 N sodium hydroxide aqueous solution. 10 g of commercially available titania (anatase titania made by Norton) was poured into this aqueous solution under stirring, and the stirring was continued for another hour while the system was kept at 65 to 70° C. and the pH at 7 to 8. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air, which gave a gold-loading carrier in which gold was supported on a titania carrier (Au/titania). The amount of gold supported here was measured and found to be 4.7 wt % with respect to the carrier. The metal particle state here was also examined, which revealed that almost all of the metal was highly dispersed in the form of particles with a diameter of 5 nm or less, and that the average particle diameter was 5 nm or less.

(2) Manufacture of Carboxylic Ester 15 mL of n-propanol and 0.5 g of the above-mentioned catalyst were sealed in a 100 mL autoclave equipped with a rotary agitator. The interior of the system was then pressurized to 0.3 MPa with oxygen, after which the temperature was raised to 80° C. under stirring, and this temperature was maintained for 5 hours. During this time the supply of oxygen was continued so as to maintain the above-mentioned internal pressure. The system was then cooled and the seal broken, and the reaction solution was analyzed, which revealed the n-propanol conversion to be 23%, and the propyl propionate (the product) selectivity and yield to be 81% and 19%, respectively.

EXAMPLE 3-10

(1) Preparation of Catalyst

A gold/zirconia catalyst was manufactured in the same manner as in Example 9 (1), except that zirconia (made by Norton) was used in place of titania as the carrier. The amount of supported gold was measured in the same manner as in Example 9 and found to be 4.4 wt % with respect to the carrier. The metal particle diameter of the catalyst was also examined, which revealed that almost all of the metals was highly dispersed in the form of particles with a diameter of 5 nm or less, and that the average particle diameter was 5 nm or less.

(2) Manufacture of Carboxylic Ester 15 mL of n-butanol and 0.5 g of the above-mentioned catalyst were sealed in a 100 mL autoclave equipped with a rotary agitator. The interior of the system was then pressurized to 0.3 MPa with oxygen, after which the temperature was raised to 90° C. under stirring, and this temperature was maintained for 5 hours. During this time the supply of oxygen was continued so as to maintain the above-mentioned internal pressure. The system was then cooled and the seal broken, and the reaction solution was analyzed, which revealed the n-butanol conversion to be 28%, and the butyl n-butyrate (the product) selectivity and yield to be 79% and 22%, respectively.

EXAMPLE 3-11

(1) Preparation of Catalyst

The entire amount of a 500 mL aqueous solution (70° C.) in which 0.88 g of tetrachloroauric acid tetrahydrate and 40.4 g of iron nitrate nonahydrate had been dissolved was poured over a period of about 1 minute under stirring into a 500 mL aqueous solution (65 to 70° C.) in which 19.6 g of sodium carbonate had been dissolved. The mixed solution thus obtained was held at 65 to 70° C. while the supernatant was removed by centrifugation. Stirring and washing with 1 L of ion exchange water (10 minutes) was repeated three times. The resulting solids were dried for 12 hours at 120° C., then calcined for 4 hours at 450° C. in air, which gave a gold-loading carrier (Au/Fe$_2$O$_3$) in which gold was supported on an iron oxide carrier. The amount of gold supported here was measured and found to be 4.8 wt % with respect to the carrier. The gold particle diameter here was also examined, which revealed that almost all of the gold was highly dispersed in the form of particles with a diameter of 5 nm or less, and that the average particle diameter was clearly 5 nm or less.

(2) Manufacture of Carboxylic Ester 1.5 g of ethyl 3-hydroxypropionate, 15 mL of ethanol, and 0.5 g of the above-mentioned catalyst were sealed in a 100 mL autoclave equipped with a rotary agitator. The interior of the system was then pressurized to 0.3 MPa with oxygen, after which the temperature was raised to 80° C. under stirring, and this temperature was maintained for 5 hours. During this time the supply of oxygen was continued so as to maintain the above-mentioned internal pressure. The system was then cooled and the seal was broken, and the reaction solution was analyzed, which revealed the ethyl 3-hydroxypropionate conversion to be 19%, and the malonic diester (the product) selectivity and yield to be 82% and 16%, respectively, on the basis of the supplied ethyl 3-hydroxypropionate.

EXAMPLE 3-12

(1) Preparation of Catalyst

A catalyst loading carrier (Au/ZnO) was prepared in the same manner as in Example 3-11 (1), except that 29.8 g of zinc nitrate hexahydrate was used in place of the 40.4 g of iron nitrate nonahydrate, and that the tetrachloroauric acid tetrahydrate and sodium carbonate were used in amounts of 0.51 g and 13.2 g, respectively. The amount of gold supported was measured in the same manner as in Example 3-9 and found to be 2.9 wt % with respect to the carrier. The gold particle diameter here was also examined, which revealed that nearly all of the gold was highly dispersed in the form of particles with a diameter of 5 nm or less, and that the average particle diameter was clearly 5 nm or less.

(2) Manufacture of Carboxylic Ester 15 mL of allyl alcohol and 0.5 g of the above-mentioned loading carrier were sealed in a 100 mL autoclave equipped with a rotary agitator. The interior of the system was then pressurized to 0.3 MPa with oxygen, after which the temperature was raised to 85° C. under stirring, and this temperature was maintained for 5 hours. During this time the supply of oxygen was continued so as to maintain the above-mentioned internal pressure. The system was then cooled and the seal broken, and the reaction solution was analyzed, which revealed the allyl alcohol conversion to be 23%, and the allyl acrylate (the product) selectivity and yield to be 76% and 17%, respectively.

EXAMPLE 3-13

(1) Preparation of Catalyst 0.5 L of a tetrachloroauric acid aqueous solution with a concentration of 20 mmol/L was kept at 65 to 70° C. while being adjusted to a pH of 7 with a 0.5 N sodium hydroxide aqueous solution. 20 g of the titanium-silica carrier obtained in Example 1-23 was poured into this aqueous solution under stirring, and the stirring was continued for another hour while the system was kept at 65 to 70° C. The system was then allowed to stand and the supernatant was removed. 0.8 L of ion exchange water was added to the remaining gold-fixed substance, and the system was stirred for 5 minutes at room temperature, after which the supernatant was removed. This washing step was repeated three times. The gold-fixed substance was filtered off and dried for 10 hours at 100° C., then calcined for 3 hours at 400° C. in air, which gave a gold-loading carrier in which gold was supported on a titanium-silica carrier (Au/titanium-SiO$_2$). The amount of gold supported was measured and found to be 3.6 wt % with respect to the Ti-silica carrier.

(2) Manufacture of Carboxylic Ester 3 g of ethylene glycol, 12 g of methanol, and 1 g of the above-mentioned carrier were sealed in a 100 mL autoclave equipped with a rotary agitator. The interior of the system was then pressurized to 0.25 MPa with oxygen and to 0.25 MPa with nitrogen for a total of 0.5 MPa, after which the temperature was raised to 90° C. under stirring, and this temperature was maintained for 6 hours. During this time the supply of oxygen was continued so as to maintain the above-mentioned internal pressure. The system was then cooled and the seal was broken, and the resultant liquid analyzed, which revealed the ethylene glycol conversion to be 82%, and the methyl glycolate (the product) selectivity and yield to be 78% and 64%, respectively, on the basis of the supplied ethylene glycol. As by-products, 2-hydroxyethyl glycolate was produced at a selectivity of 18% and dimethyl oxalate at a selectivity of less than 1%, and methyl formate was produced in a molar ratio of 0.12 with respect to the methyl glycolate.

EXAMPLE 3-14

(1) Preparation of Catalyst

TiO$_2$—ZrO$_2$ was prepared by coprecipitation (Ti:Zr=1:1 (molar ratio), calcination temperature: 600° C., 50 to 250 mesh). Gold was supported on this powder by the same operation as in Example 3-13, which gave a gold/TiO$_2$—ZrO$_2$ carrier. 4 g of the above-mentioned carrier was then added to a 15 mL methanol solution containing 0.367 g of lead acetate trihydrate, and the methanol was removed at 80° C. and normal pressure with an evaporator. This product comprised the carrier impregnated with lead acetate. A glass tube was then packed with 4 g of this product, and a hydrogen reduction treatment was conducted for 3 hours at 400° C. while a mixed gas of hydrogen and nitrogen (hydrogen:nitrogen=1:9 (volumetric ratio)) was passed through. This gave a catalyst loading carrier in which fine particles containing gold and lead were supported on a TiO$_2$—ZrO$_2$ carrier. The amounts of gold and lead supported here were measured and found to be 5.8 wt % and 4.9 wt %, respectively.

(2) Manufacture of Carboxylic Ester

An oxidation reaction was carried out by the same operation as in Example 3-13, except that 2.25 g of ethylene glycol was used. As a result, the ethylene glycol conversion was 93%, and the methyl glycolate (the product) selectivity and yield were 85% and 77%, respectively, on the basis of the supplied ethylene glycol. As by-products, 2-hydroxyethyl glycolate was produced at a selectivity of 11% and dimethyl oxalate at a selectivity of less than 1%, and methyl formate was produced in a molar ratio of 0.24 with respect to the methyl glycolate.

EXAMPLE 3-15

This example involves the successive addition of an alcohol.

2 g of ethylene glycol, 24 g of methanol, and 1.5 g of the Au—Pb/$TiO_2$—$ZrO_2$ catalyst obtained in Example 3-14 were sealed in a 100 mL autoclave equipped with a rotary agitator. The interior of the system was then pressurized to 0.25 MPa with oxygen and to 0.25 MPa with nitrogen for a total of 0.5 MPa, after which the temperature was raised to 90° C. under stirring, and the reaction was conducted for 2 hours while the supply of oxygen was continued so that the above-mentioned internal pressure would be maintained at 0.5 MPa. 4 g of ethylene glycol was then added to the autoclave over a period of 2 hours using a feed pump, after which the reaction was conducted for another 2 hours under stirring at 90° C. while the supply of oxygen was continued so that the above-mentioned internal pressure would be maintained at 0.5 MPa. The system was then cooled and the seal was broken, and the reaction liquid was analyzed, which revealed the ethylene glycol conversion to be 93%, the methyl glycolate selectivity and yield to be 89% and 95%, respectively, on the basis of the supplied ethylene glycol. As by-products, 2-hydroxyethyl glycolate was produced at a selectivity of 8% and dimethyl oxalate at a selectivity of less than 1%, and methyl formate was produced in a molar ratio of 0.26 with respect to the methyl glycolate.

EXAMPLE 3-16

An oxidation reaction was conducted by the same operation as in Example 3-13, except that 3 g of 1,2-propylene glycol was used in place of the ethylene glycol. As a result, the 1,2-propylene glycol conversion was 88%, and the methyl pyruvate (the product) selectivity and yield were 66% and 58%, respectively, on the basis of the supplied 1,2-propylene glycol, while the methyl lactate selectivity and yield were 12% and 11%, respectively. Acetol was produced at a selectivity of 20% as a by-product.

The invention claimed is:

1. A method for producing a carboxylic ester comprising reacting oxygen, an aldehyde and an alcohol in the presence of a catalyst for the preparation of a carboxylic ester which comprises a carrier and 1) ultrafine gold particles or 2) ultrafine metal particles containing gold and a second element other than gold,
wherein the particles are supported on the carrier,
wherein the atomic ratio of gold to the second element is no less than 1:10,
and wherein the reaction is a liquid phase reaction.

2. The method according to claim 1, wherein the aldehyde is at least one member of the group consisting of acrolein and methacrolein, and the alcohol is at least one member of the group consisting of $C_1$ to $C_4$ primary alcohols.

3. The method according to claim 1, wherein the aldehyde is at least one member of the group consisting of glyoxal and pyruvic aldehyde, and the alcohol is at least one member of the group consisting of $C_1$ to $C_4$ primary alcohols.

4. A method for producing a carboxylic ester comprising reacting oxygen and one or more types of alcohol in the presence of a catalyst for the preparation of a carboxylic ester which comprises a carrier and 1) ultrafine gold particles or 2) ultrafine metal particles containing gold and a second element other than gold,
wherein the particles are supported on the carrier,
wherein the atomic ratio of gold to the second element is no less than 1:10,
and wherein the reaction is a liquid phase reaction.

5. The method according to claim 4, wherein at least one of the types of alcohol is ethylene glycol or 1,2-propylene glycol.

6. The method for the preparation of a carboxylic ester according to claim 1 or claim 4, wherein the second element is at least one member selected from the group consisting of elements in groups 2B, 3B, 4B, 5B and 6B of the fourth to sixth periods of the Periodic Table, and group 4 of the fourth period of the Periodic Table.

7. The method for the preparation of a carboxylic ester according to claim 1, wherein the carrier is an inorganic oxide.

8. The catalyst for the preparation of a carboxylic ester according to claim 1 or claim 4, wherein the carrier is composed of an oxide including at least one member of the group consisting of silicon, magnesium, calcium, strontium, barium, aluminum, titanium, vanadium, chromium, manganese, iron, cobalt, nickel, copper, zinc, zirconium, niobium, tin, lead, lanthanum and cerium.

9. The method for the preparation of a carboxylic ester according to claim 4, wherein the carrier is an inorganic oxide.

10. The catalyst for the preparation of a carboxylic ester according to claim 4, wherein the carrier is composed of an oxide including at least one member of the group consisting of silicon, magnesium, calcium, strontium, barium, aluminum, titanium, vanadium, chromium, manganese, iron, cobalt, nickel, copper, zinc, zirconium, niobium, tin, lead, lanthanum and cerium.

11. The method of either claim 1 or claim 4, wherein the metal particles of said catalyst consists of said ultrafine gold particles or ultrafine metal particles containing gold and a second element other than gold.

* * * * *